(12) United States Patent
Nakao

(10) Patent No.: US 7,775,989 B2
(45) Date of Patent: Aug. 17, 2010

(54) NEEDLE BIOPSY FORCEPS WITH INTEGRAL SAMPLE EJECTOR

(75) Inventor: Naomi L. Nakao, New York, NY (US)

(73) Assignee: Granit Medical Innovations, LLC, New York, NY (US)

(*) Notice: Subject to any disclaimer, the term of this patent is extended or adjusted under 35 U.S.C. 154(b) by 689 days.

(21) Appl. No.: 10/655,087

(22) Filed: Sep. 3, 2003

(65) Prior Publication Data

US 2005/0049520 A1  Mar. 3, 2005

(51) Int. Cl.
*A61B 10/00* (2006.01)
*A61B 17/32* (2006.01)
*A61B 17/00* (2006.01)

(52) U.S. Cl. ............... 600/564; 600/566; 600/567; 606/167; 606/205; 606/207

(58) Field of Classification Search ............... 600/566, 600/567, 564; 606/167, 205, 207
See application file for complete search history.

(56) References Cited

U.S. PATENT DOCUMENTS

| | | | | |
|---|---|---|---|---|
| 4,607,619 A * | 8/1986 | Seike et al. | | 600/106 |
| 4,817,630 A * | 4/1989 | Schintgen et al. | | 600/564 |
| 4,887,612 A * | 12/1989 | Esser et al. | | 600/564 |
| 5,133,727 A * | 7/1992 | Bales et al. | | 606/170 |
| 5,238,002 A * | 8/1993 | Devlin et al. | | 600/564 |
| 5,249,583 A * | 10/1993 | Mallaby | | 600/567 |
| 5,373,854 A * | 12/1994 | Kolozsi | | 600/562 |
| 5,573,546 A * | 11/1996 | Nakao | | 606/205 |
| 5,762,069 A * | 6/1998 | Kelleher et al. | | 600/564 |
| 5,810,876 A * | 9/1998 | Kelleher | | 606/205 |
| 5,823,971 A * | 10/1998 | Robinson et al. | | 600/567 |
| 5,840,044 A * | 11/1998 | Dassa et al. | | 600/567 |
| 6,066,102 A * | 5/2000 | Townsend et al. | | 600/564 |
| 6,129,683 A * | 10/2000 | Sutton et al. | | 600/564 |
| 6,142,957 A * | 11/2000 | Diamond et al. | | 600/567 |
| 6,149,607 A * | 11/2000 | Simpson et al. | | 600/567 |
| 6,273,860 B1 * | 8/2001 | Kostylev et al. | | 600/564 |
| 6,368,327 B2 * | 4/2002 | Lippitt et al. | | 606/110 |
| 6,544,271 B1 * | 4/2003 | Adams et al. | | 606/139 |
| 6,572,578 B1 * | 6/2003 | Blanchard | | 604/22 |
| 6,764,499 B2 * | 7/2004 | Honey et al. | | 606/207 |
| 6,846,292 B2 * | 1/2005 | Bakry | | 600/564 |
| 6,984,213 B2 | 1/2006 | Horner et al. | | |
| 2005/0049520 A1 * | 3/2005 | Nakao | | 600/562 |

* cited by examiner

*Primary Examiner*—Max Hindenburg
*Assistant Examiner*—Jeffrey G Hoekstra
(74) *Attorney, Agent, or Firm*—R. Neil Sudal; Henry D. Coleman; William J. Sapone

(57) ABSTRACT

A sample ejecting safety biopsy needle forceps includes a pair of pivotable cups and a sample-spearing needle disposed between the jaws for holding multiple specimens. A tissue sample-contacting surface at a proximal end of a needle is movable relative to the needle to contact the samples and push them along the needle when the cups are in an open position. A control or actuator at a proximal end of the forceps accomplishes the relative movement.

4 Claims, 31 Drawing Sheets

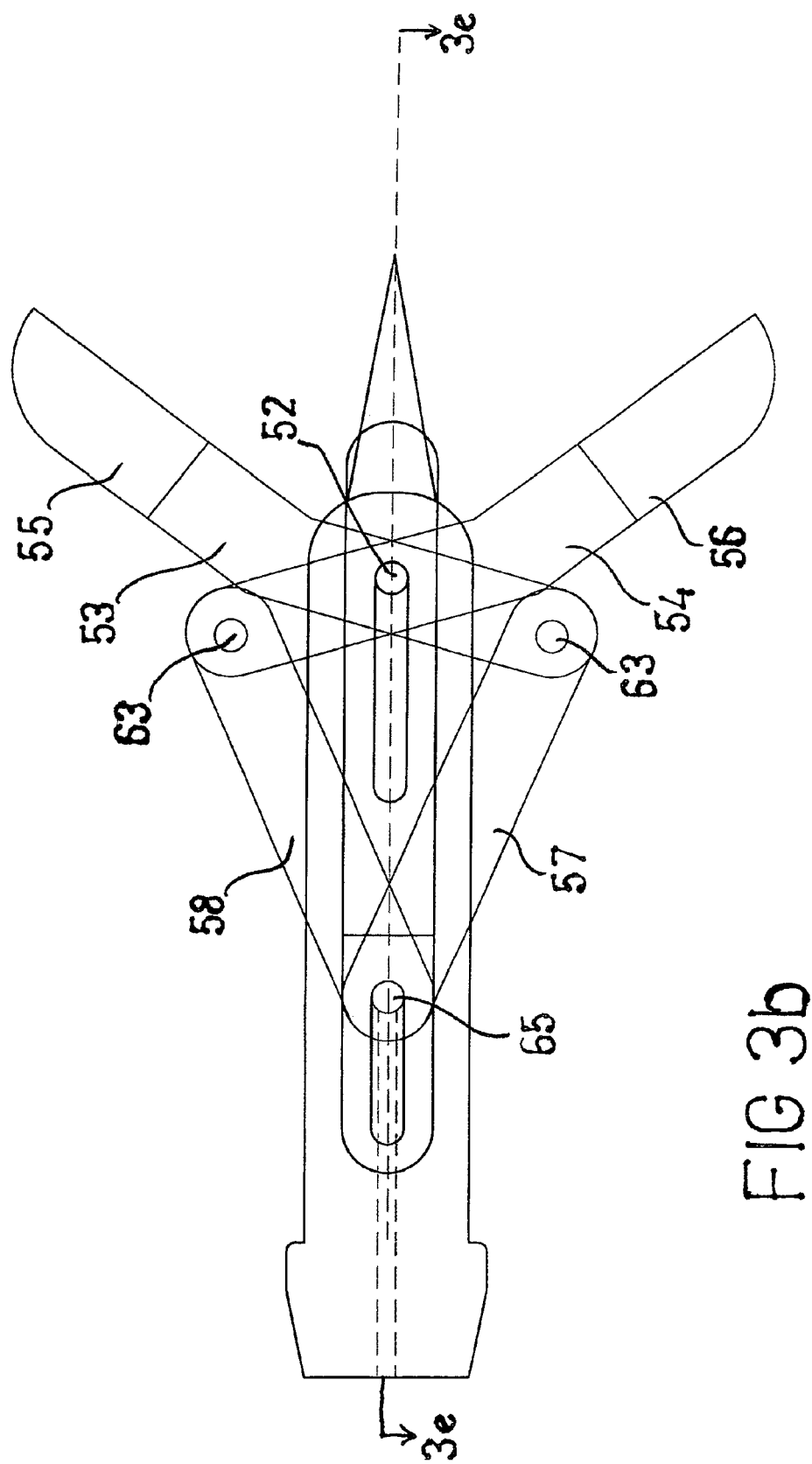

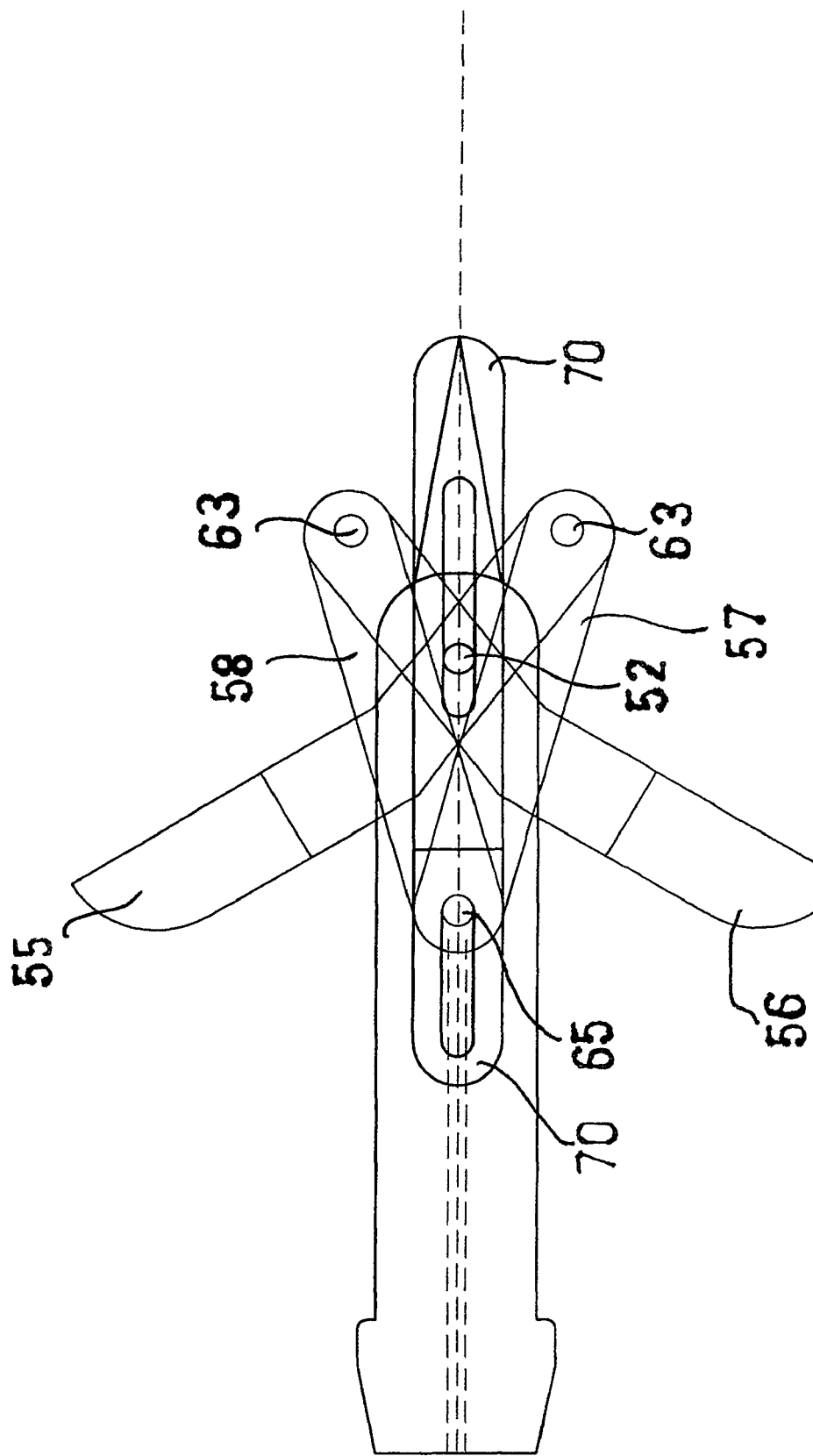

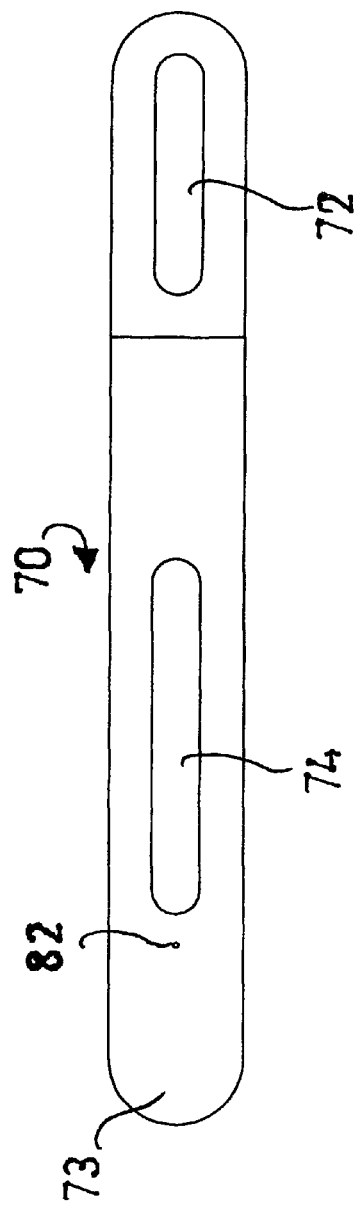
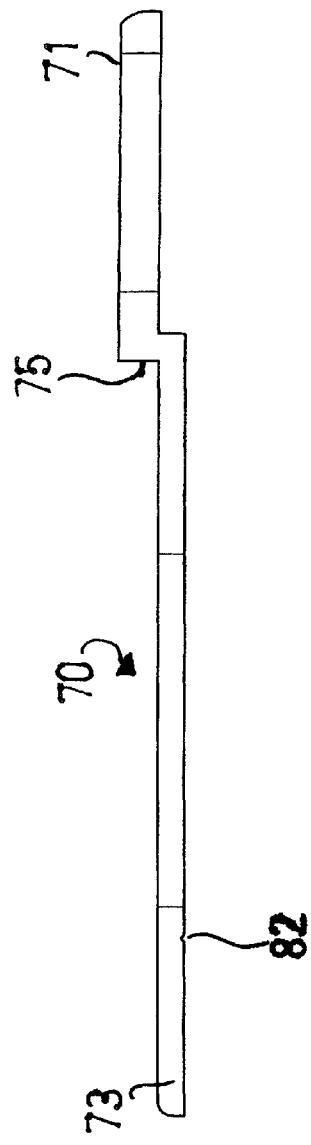

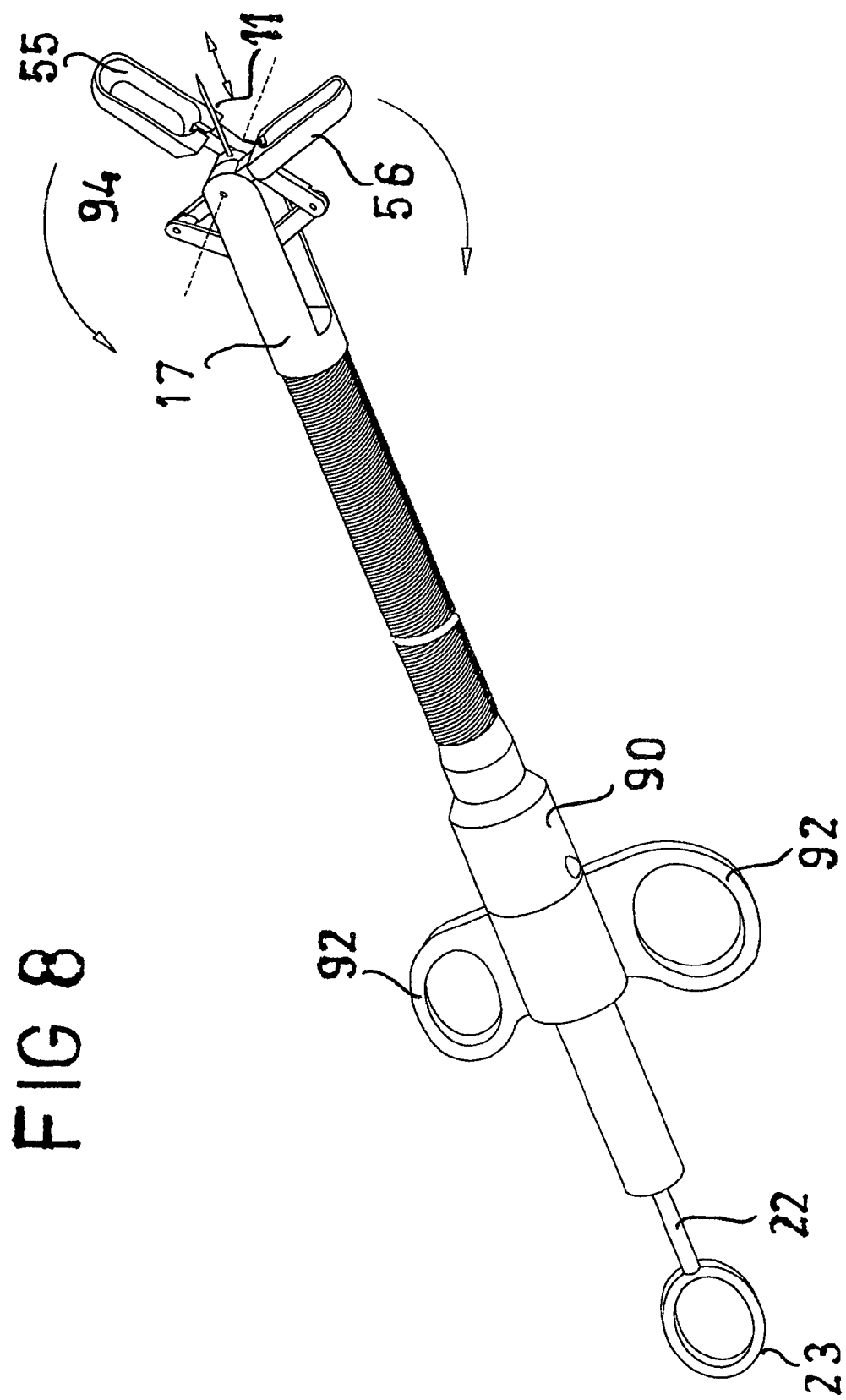

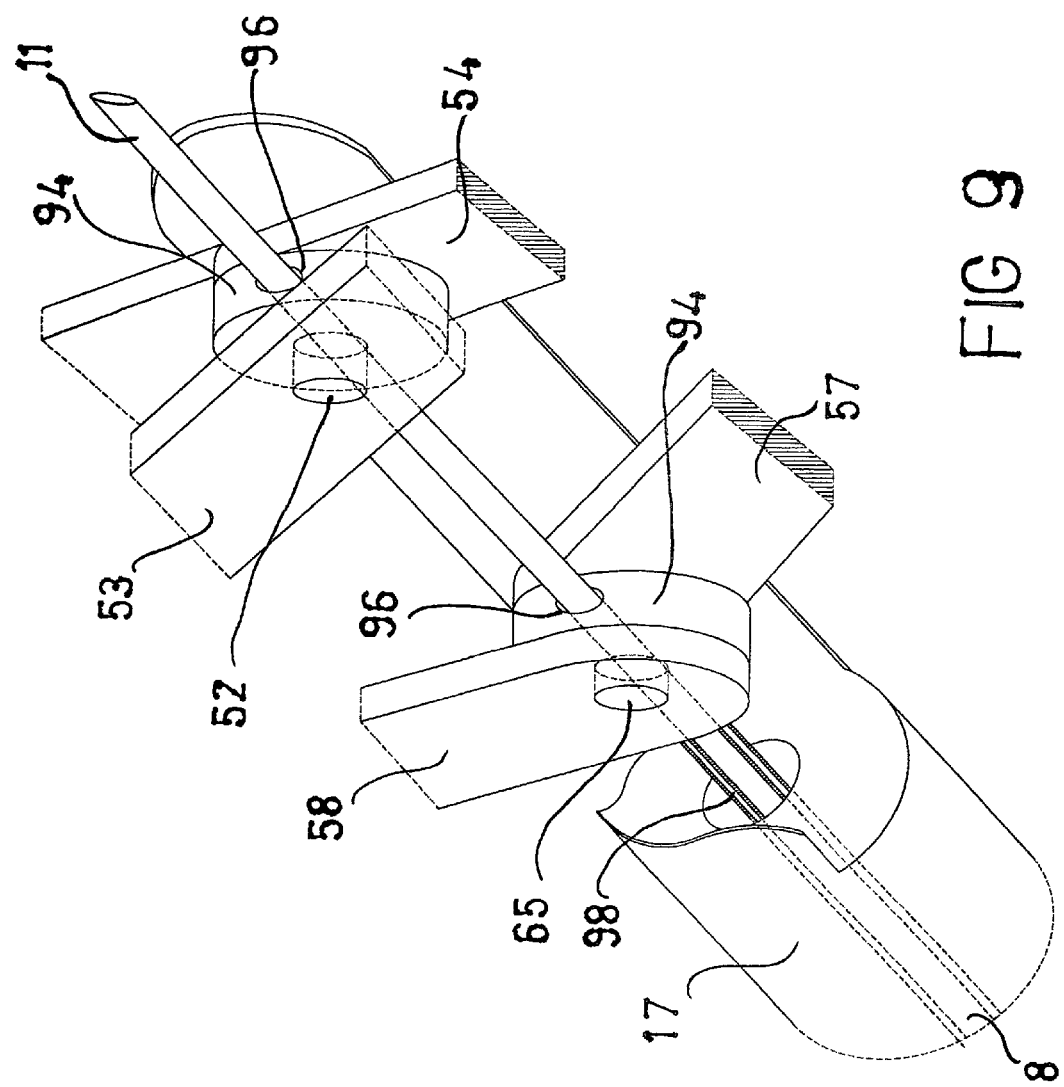

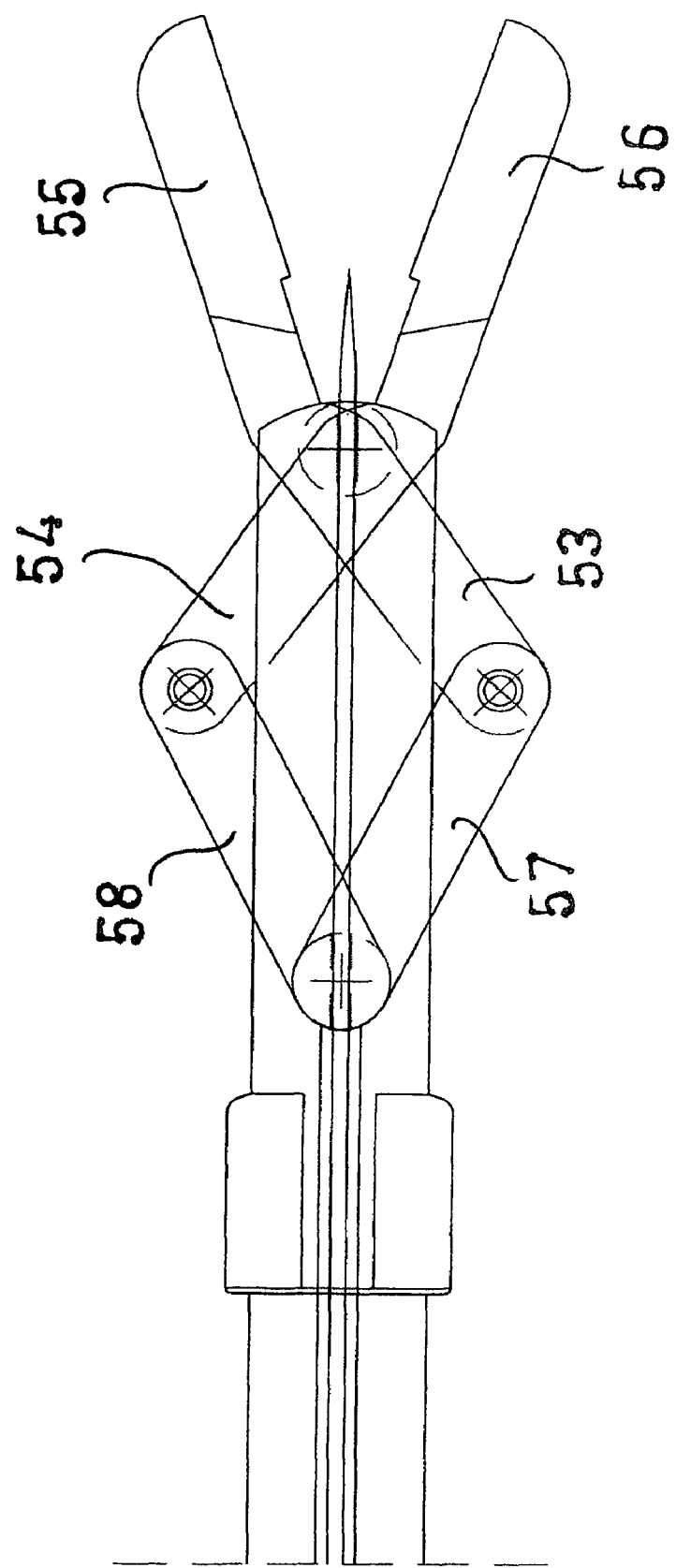

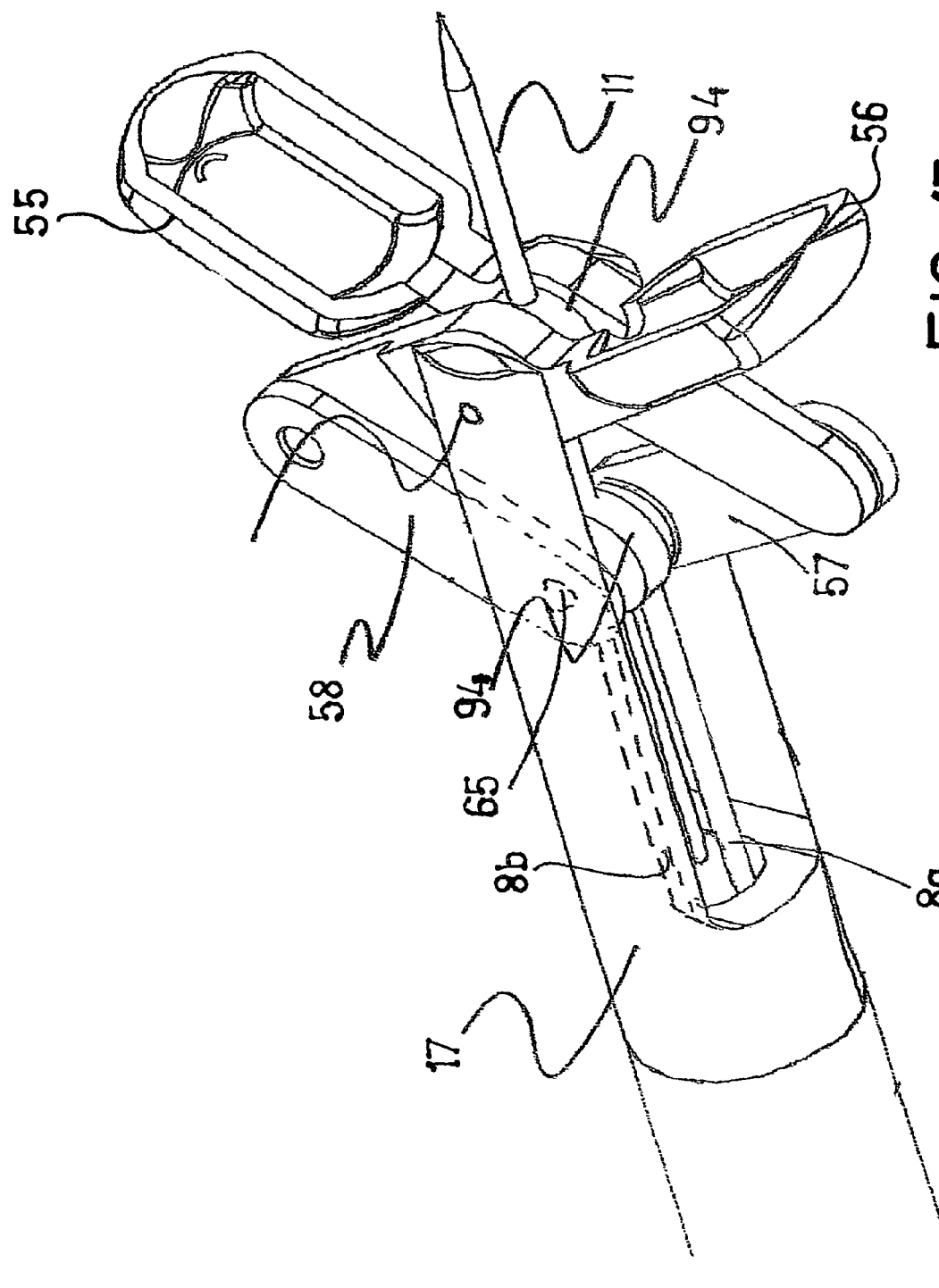

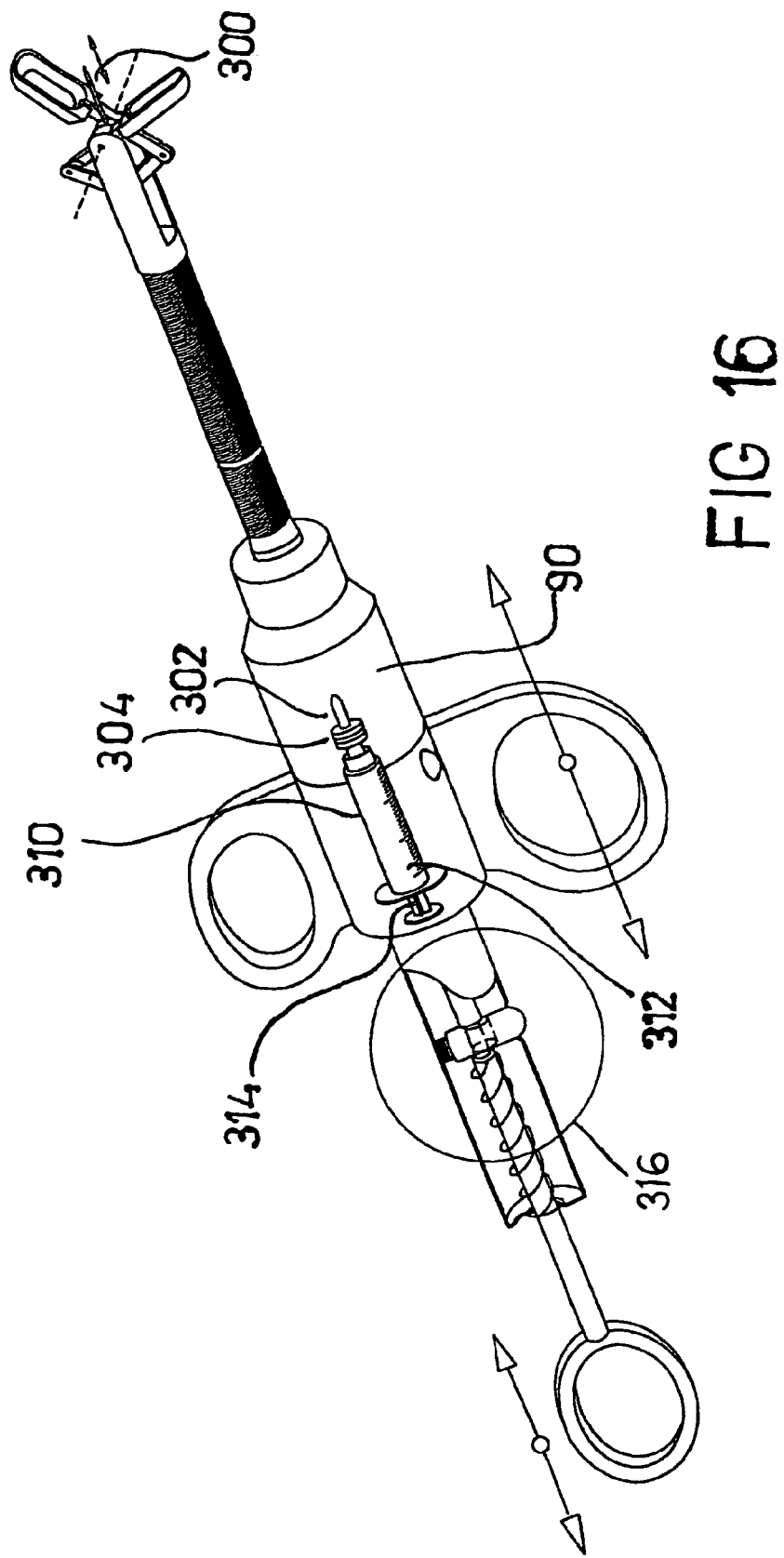

NEEDLE BIOPSY FORCEPS WITH INTEGRAL SAMPLE EJECTOR

FIELD OF THE INVENTION

The invention relates to flexible biopsy forceps used in conjunction with an endoscope and rigid forceps used with a laparoscope for retrieval of a tissue sample from the interior of a patient's body, where the forceps include a needle that passes through the tissue to be sampled in order to retain one or more severed samples for retrieval.

BACKGROUND OF THE INVENTION

Flexible needle biopsy forceps are used in conjunction with a fiber optic endoscope as follows: the endoscope is inserted into the stomach, colon or other hollow organ of the patient's body, an abnormality is visualized, and the flexible biopsy forceps is introduced through the biopsy channel of the endoscope. The distal end of the biopsy forceps is comprised of two opposed sharp-edged cups that are operably attached by means of pivot arms to a wire passing on the interior of a flexible cable. A fixed spike or needle is positioned within the closed cups. As used hereinafter, the term "needle" will be understood to include both a needle and a spike, or other similar member that passes through and retains the severed tissue sample until the forceps are removed from the patient's body. Actuation means, such as thumb and/or finger grips or a spool, are operably connected to the proximal ends of the flexible cable and the one or more wires are used to move the cups between an open and closed position.

When the forceps' distal end is properly positioned at the sampling site, the cups are moved to the open position, the needle makes contact with and penetrates the tissue to be sampled and the cups are then closed on the tissue, grasping and severing a sample of tissue that is held on the needle within the closed cups while the forceps is withdrawn from the patient.

The rigid forceps are employed in conjunction with the laparoscopic procedure in a similar manner. With both types of the device, after the forceps has been removed from the endoscope, the tissue sample or samples must then be removed from the needle and placed into an appropriate receptacle that contains a preservative (e.g., formalin). In many instances, it is difficult to safely remove the sample from the forceps needle. The physician or assisting personnel will typically use another needle or small implement to slide the tissue down and off the end of the needle.

This task is difficult and cumbersome in itself, and dangerous since there are occasions in which medical personnel have been stuck by the needle. If the patient is infected with the HIV virus, or hepatitis, or another contagious disease, the physician or assistant can be infected as well. An additional risk to the medical personnel from an infectious sample is posed by the sharp cutting edges of the cups themselves, which must be maintained in the open position while the tissue sample(s) are removed from the forceps needle.

It is therefore an object of the present invention to provide an improved needle biopsy forceps that will eject the biopsy sample from the needle or spike into a convenient receptacle by manipulation of interconnected control means at the proximal end of the forceps.

It is another object of this invention to provide an improved needle biopsy forceps having means for removing the tissue sample that can be incorporated into forceps of current construction and whose method of operation will be safe and easy to learn.

Another object of the invention is to provide tissue sample ejecting needle biopsy forceps that are easy to use and that operate in the same manner to collect and sever tissue samples as the prior art forceps.

A further object of the invention is to provide an improved needle biopsy forceps from which the tissue sample can be safely ejected without having the medical personnel directly contact or manipulate the distal end of the forceps and which will eliminate the need for such personnel to use needles or other "sharps" to collect the sample.

These and other objects are met by the improved needle biopsy forceps that are described below.

BRIEF DESCRIPTION OF THE INVENTION

As broadly contemplated, the sample ejecting safety biopsy needle forceps of the invention comprises a tissue sample contacting surface located at the proximal end of the needle and means for producing relative movement between this surface and the needle to thereby contact the sample and push it along the longitudinal axis of the needle when the cups are in the open position after removal from the hollow cable. This allows the physician or an assistant to safely and precisely deposit the sample in a container for later analysis. The relative movement is accomplished by control means located at the proximal end of the forceps. The control means preferably comprises the handle or, alternatively, is positioned near the handle. At least one linking member is slidably disposed in a hollow cable and extends from the control means in the handle to the proximal end of the instrument.

In one preferred embodiment, the tissue sample contacting surface is located outside of, and proximally displaced from the cups while the cups are closed and partially opened to sever the tissue sample. Control means at the proximal end of the forceps are manually actuated to provide, via the linking member, relative movement between the needle and the sample contacting surface to contact and dislodge the sample by slidingly advancing the sample to the tip of the needle when the cups are moved to a more fully opened position.

In another preferred embodiment, the tissue sample contacting surface is located between the cups at the juncture of the cup supporting pivot arms, and the contact surface moves along the longitudinal axis of the needle or spike when the cups are fully opened to thereby contact and dislodge the sample.

In a further preferred embodiment, the needle itself is moveable and is attached to a wire linking member and thereby to a control handle located at the proximal end of the forceps. As the wire is withdrawn proximally, so the needle is likewise withdrawn to bring the sample into contact with the contacting surface.

In another preferred embodiment, the sample contacting surface is formed on a longitudinally moveable plate attached to a wire and control means at the proximal end of the forceps. The needle is stationary and the plate moves up the axis of the needle to contact and slide the sample off the tip of the needle.

The above embodiments can also be combined with a fluid reservoir and injection system in communication with a hollow needle and/or a cauterization circuit and controls connected to the cups.

In each embodiment, the sample ejecting means is remotely activated by control means located at the proximal end of the forceps by the axial movement of an axially extending, inextensible, but flexible linking member located in the flexible cable that is secured to the distal and proximal ends of the forceps assembly. The linking member is comprised of one or more wires, a coiled wire cable that can be slidably moved within the hollow exterior cable. The proximal remote control means can be provided with a biasing force that remains armed until manually released.

As used herein, the term "wire" is to be understood to include a single strand or rod, a coiled wire cable made of metal and polymeric materials, or other suitable device.

As will be understood by one of ordinary skill in the art, the method and apparatus of the invention is applicable to, and can be adapted for use with other medical instruments and is not to be construed as limited solely to biopsy forceps.

BRIEF DESCRIPTION OF THE DRAWINGS

FIG. 3b is a view similar to FIG. 3a in a partially opened position;

FIG. 3c is a view similar to FIG. 3a in a fully opened position;

FIG. 3d is a cross-sectional view taken along line 3d-3d of FIG. 3a;

FIG. 4 is a top plan view of a sliding plate member shown in FIG. 3a;

FIG. 5 is a side elevation view of the plate of FIG. 4;

FIG. 6a is an enlarged side elevation view of a portion of spike shown in FIG. 3a;

FIG. 8 is a perspective view of biopsy forceps with cups in an open position illustrating another embodiment of the invention;

FIG. 9 is an enlarged schematic, partially cut-away and phantom view of the needle reciprocating mechanism for use in the forceps of FIG. 8;

FIG. 10b is a view similar to FIG. 10a in an open position with the needle partially withdrawn;

FIG. 15A is a front left and top perspective view of the distal end of yet another embodiment of the invention;

FIG. 16 is a perspective view of a further preferred embodiment of the invention having fluid injecting means;

DESCRIPTION OF THE PREFERRED EMBODIMENTS

Figure 1:
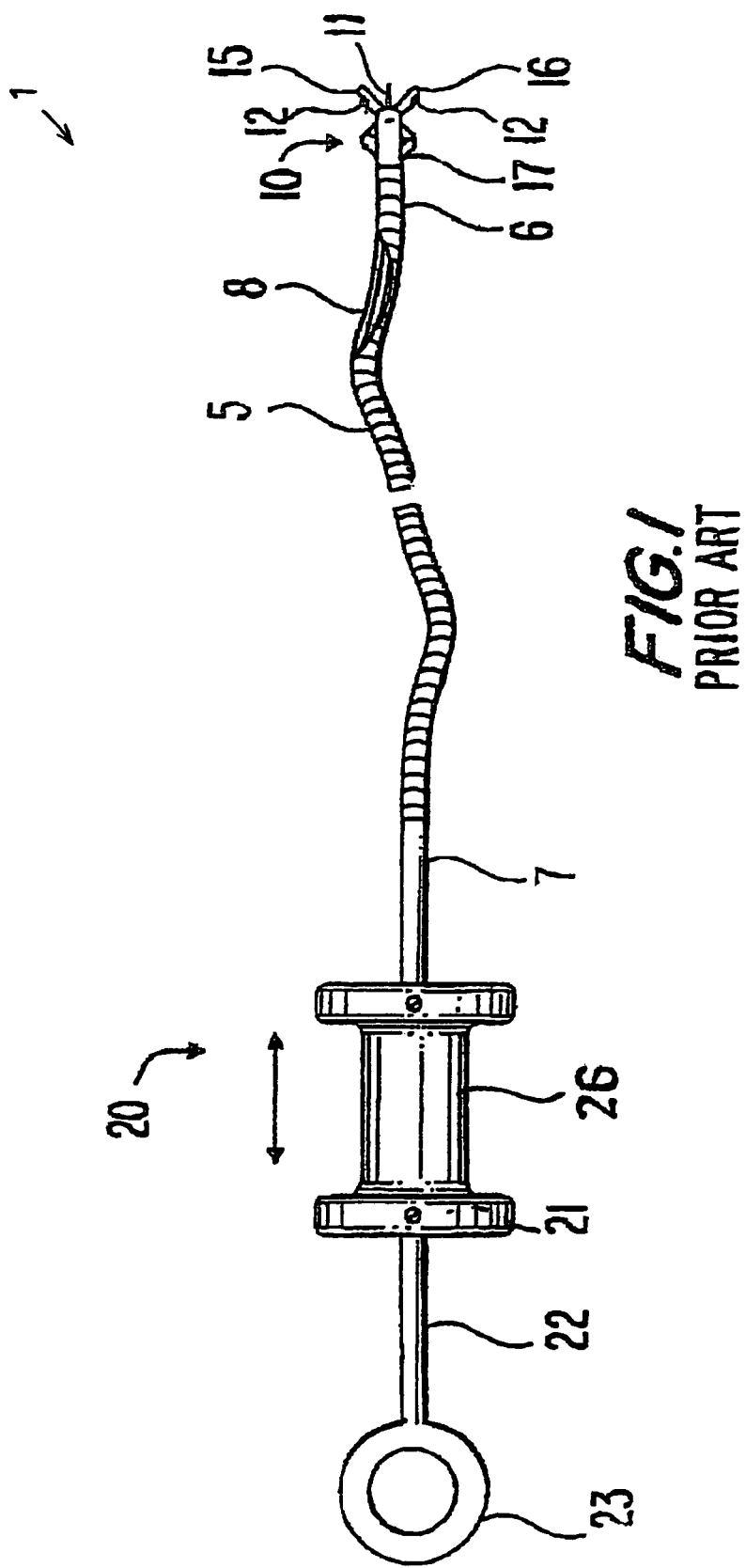
FIG. 1 is a partially cut-away side elevation view of a conventional biopsy forceps of the prior art.

A conventional needle biopsy forceps 1 of a type known in the art is illustrated in FIG. 1. The forceps comprises a hollow, flexible cable 5 having a distal end 6 and a proximal end 7. An actuating wire 8 is slidably disposed within the cable and extends from the distal to the proximal ends of the cable. At the distal end of the cable is a tissue sample collection means 10, typically comprising two opposing cups 15 and 16 pivotally attached to a clevis 17 depending from the cable 5. A needle or spike 11 extends from the distal end and is enclosed by cups 15 and 16 when they are in the closed position. The cups are operably attached to the wire 8, so that sliding the wire distally opens the cups, and sliding the wire proximally closes the cups.

With continuing reference to FIG. 1, there is shown at the proximal end 7 of the flexible external cable 5 an actuation handle means 20, typically comprising a spool 26 with flanges 21 slidably mounted on shaft 7. The shaft 22 has a thumb grip 23 depending from its proximal end. The cable 5 is mounted to the shaft 7. The wire 8 is operably attached to the spool 21, so that an axial sliding movement of the spool 21 on the shaft 22 will produce a similar movement of the wire 8 within the cable 5, thus opening and closing the cups 15 and 16.

Needle 11 is positioned inside the closed cups and is exposed when the cups are open. Needle 11 thus has a most distal position inside the space defined or enclosed by the closed cups. The opposing edges of the cups are sharpened. When the biopsy forceps is in use, a surgeon opens and closes the cups 15 and 16 by sliding the spool 21 on the shaft 22. As the cups are moved into position relative to the tissue to be sampled, the centrally positioned needle penetrates the sample. The sharpened edges of the cup engage the tissue and sever a small sample which is retained in the cavity formed by the closed cups. Holes 12 are commonly provided in the cups 15 and 16 to permit fluid to drain from the cups.

During most procedures two or more biopsies are taken and stacked on the shaft of the needle, thereby allowing multiple biopsies to be taken in a single pass. As explained above, a tissue sample can be difficult to dislodge from its position on the needle 11 and a small sharp implement, such as another needle, must be manually applied by medical personnel to pry the sample from the distal end of the needle. The present invention provides a significant improvement to the safety of personnel who are otherwise exposed to the risk of being stuck by the needle or spike or being cut by the sharp edges of the cups all of which are contaminated with the bodily fluids of the patient from whom the samples were removed.

Referring now to FIGS. 2-7, one preferred embodiment of the improved tissue sample ejection means 50 of the present invention for use in needle biopsy forceps is schematically illustrated. With reference to FIG. 3A, there is illustrated the distal end of the forceps that includes a stationary sample retaining spike 11 inside closed cups 55 and 56. Scissor arms 53, 57 and 54, 58 are pivotally mounted at pivot pins 52, 63 and 65 and operably joined to open and close cups 55, 56 in response to movement of rod 8 as actuated by thumb ring 23.

The instrument of the invention is preferably constructed for use with existing endoscopes having working channels of 2.8 mm or 3.2 mm and a length of 230 cm. The wires utilized for controlling the movement of the various elements are preferably 0.010 inch diameter. In an especially preferred embodiment, the wire or wires pass through a support tube of thin walled polymeric material having an outside diameter of 0.023 inch, which reduces frictional effects inside the spiral-wound cable extending from the control means 20 at the proximal end.

The distal ends of the levers 57 and 58 are pivotally attached to the proximal ends of the scissor links or arms 53 and 54, respectively, by pins 63. It will be understood that by sliding the wire 8 in the distal direction relative to the cable 5, the distance between the pivot pins 52 and 65 is reduced, toggling the pivot pins 63 outward. The resulting pivoting motion of the levers or scissor arms 53, 54, 57 and 58 opens the cups 55 and 56.

Sliding activator plates 70, also illustrated in FIGS. 4 and 5, are slidably mounted on either side of fixed spike 11 and it backing plate portion. Plates 70 are each provided with proximal slot 72 and distal slot 74 for receiving pivot posts or pins 65 and 52, respectively. Pivot post 65 is attached to rod 8, as by a yoke or L-bracket, and when it is advanced distally, as illustrated in FIG. 3B, initiates movement of the cups to a partially open position. As pivot post 65 continues to advance distally, the actuator plates 70 advance along the longitudinal axis of flanking spike 11 until, as shown in FIG. 3C, the distal end portions 73 of each of plates 70 are positioned at either side of the tip of spike 11.

As will be apparent to one skilled in the art, those elements which are described as having been formed from the flattened end of the actuating wire or wires 8, and therefore integral with the wire, can also be fabricated as a separate element and thereafter welded or otherwise secured to the end of the wire.

Thus, in this embodiment, the distal end portion 73 of plates 70 provides a sample contacting surface to controllingly contact and slide the sample S off the tip end of spike 11 and into a receiving container.

In a particularly preferred embodiment of this aspect of the apparatus, engagement means are provided to limit the relative movement between the spike 11 and sliding plates 70. The engagement means prevents inadvertent relative movement between the needle and sample contacting surface so that the sample is not pushed off the needle before the user is ready to place the sample in a container. The restraining engagement means can include projecting a ball or sphere in the central portion of the spike and a corresponding detent or recess in one or both adjacent side plates 70. One suitable arrangement is schematically illustrated in the exploded detail of FIGS. 6a and 6b where ball 80 is positioned in spike 11 to be received in corresponding recess 82 in plate 70 to thereby stop the advance of the plate. Alternative constructions, e.g., a dimpled projection and matching detent or recess in the members 11 and 70, or in another stationary member, can be utilized to stop the relative movement at a predetermined position. The force required to reverse the position of the plates 70 can be predetermined to assure smooth operation by the user.

Figure 2:
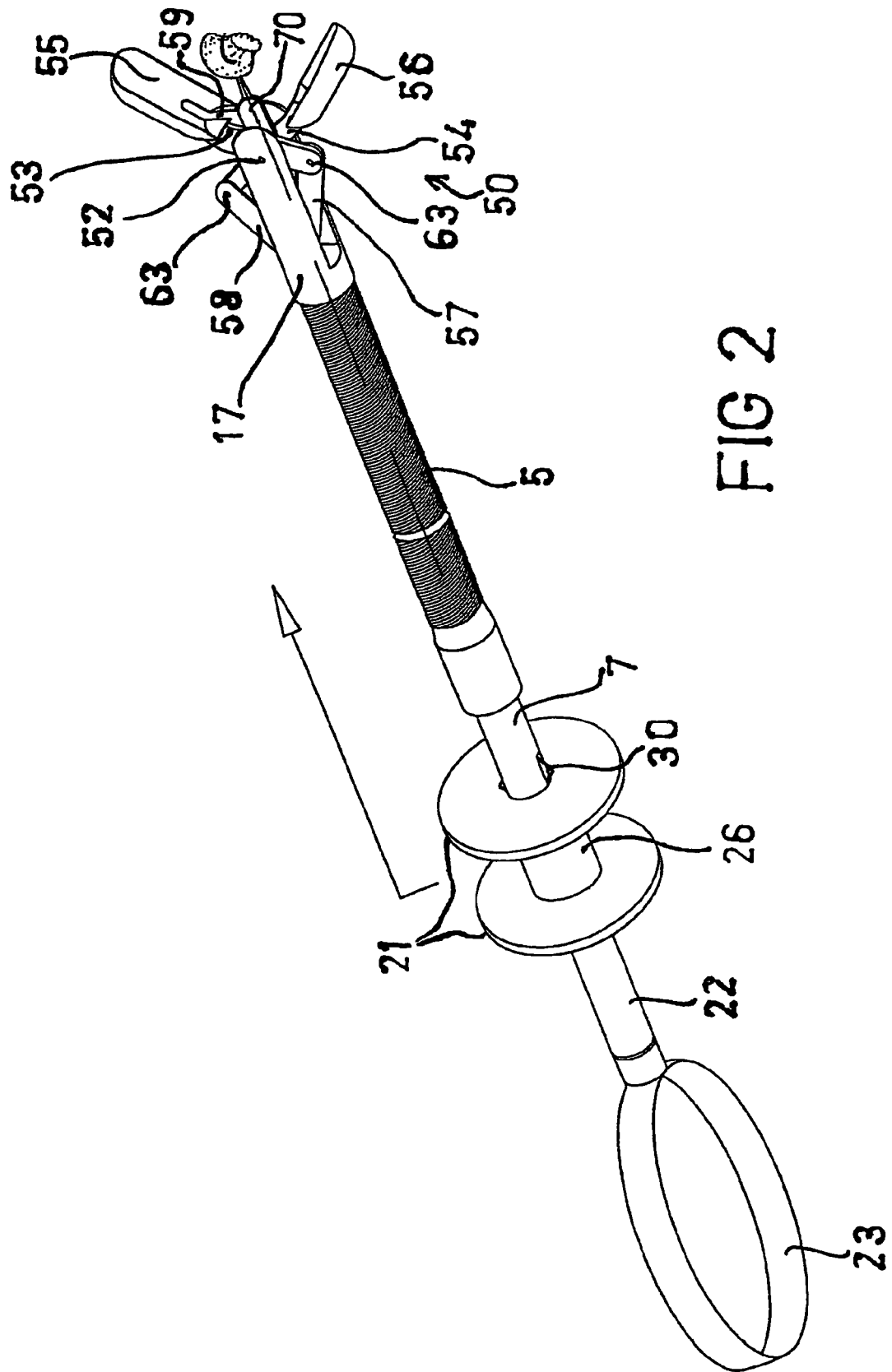
FIG. 2 is a perspective view of one preferred embodiment of the forceps of the invention, in a partially opened position.
Figure 7A:
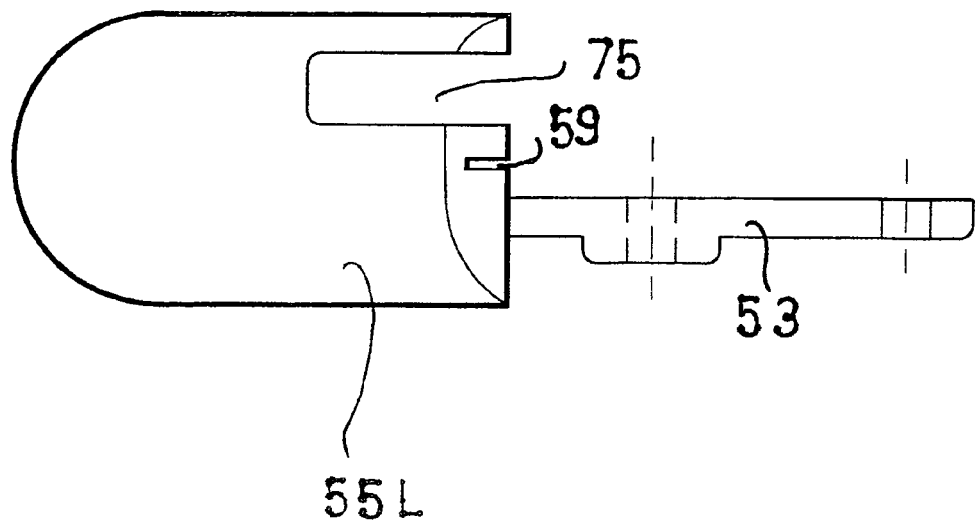
FIG. 7a is a top plan view of a cup and supporting arm for use in one embodiment of the invention.
Figure 7B:
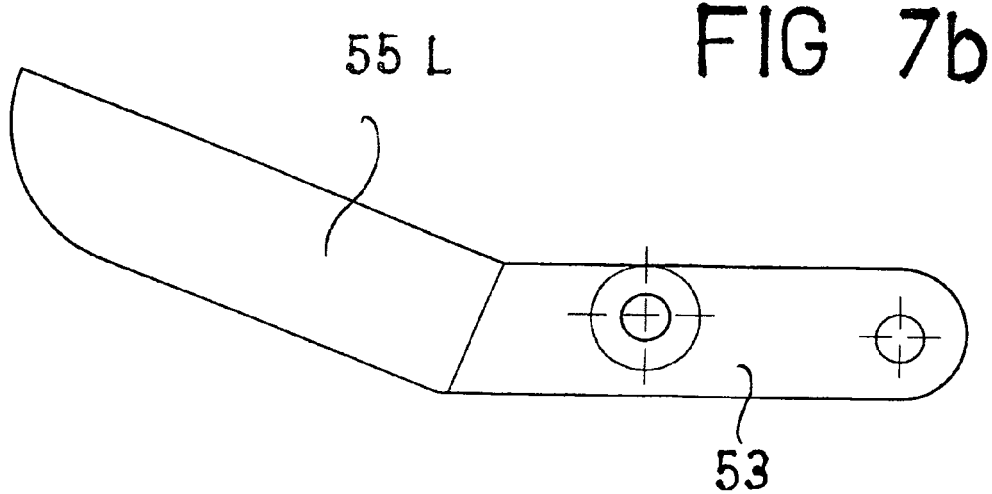
FIG. 7b is a side elevation view of the cup of FIG. 7b.

As illustrated in FIG. 2, cups 55, 56 are provided with a groove 59 to receive the shaft or blade of the spike 11. It will also be understood that a smaller notch or groove opening can be provided for a needle. If a larger cup is to be utilized with the forceps, an additional and wider opening may be required to accommodate the scissor arms when the cups are extended to open beyond 180 degrees. A suitable construction is illustrated in FIG. 7a for a larger cup 55L having opening 75 adapted to receive the scissor arms.

The biopsy forceps is inserted into the working channel of the endoscope to be controlled by external handle assembly 20. When the biopsy is to be taken, a sliding member in the form of spool 26 provided with spaced flanges 27 is pushed distally with the index and middle fingers, the thumb being moved in the thumb ring 23.

A stop element 30 is provided distally of the spool 20 to limit its forward movement and, optionally, to releasably lock it in the forward position. When the spool 26 is pushed, the rod is moved distally. Since it is connected to the moving pivot, it moves the scissor links thereby opening the cups 55, 56. The plates 70 stay in place because of the proximal hole 74 in them. When the biopsy is to be obtained, the movement of the sliding spool, is prevented by the proximal spring. A biopsy sample S is obtained by closing the cups to sever the tissue and the forceps is moved away from that location. Additional biopsy samples can be collected and stacked one against the other along the needle.

After the instrument has been removed from the endoscope's channel to a position outside the body, the specimen is dislodged into the preservative solution by pushing the thumb ring 23 with enough force to overcome the biasing force of the spring. When this is done, rod 8 begins to move the contacting surfaces distally. The cups open to the ejection position while the contacting surfaces of plates 70 slide up the needle to push the specimen off the needle.

Figure 3A:
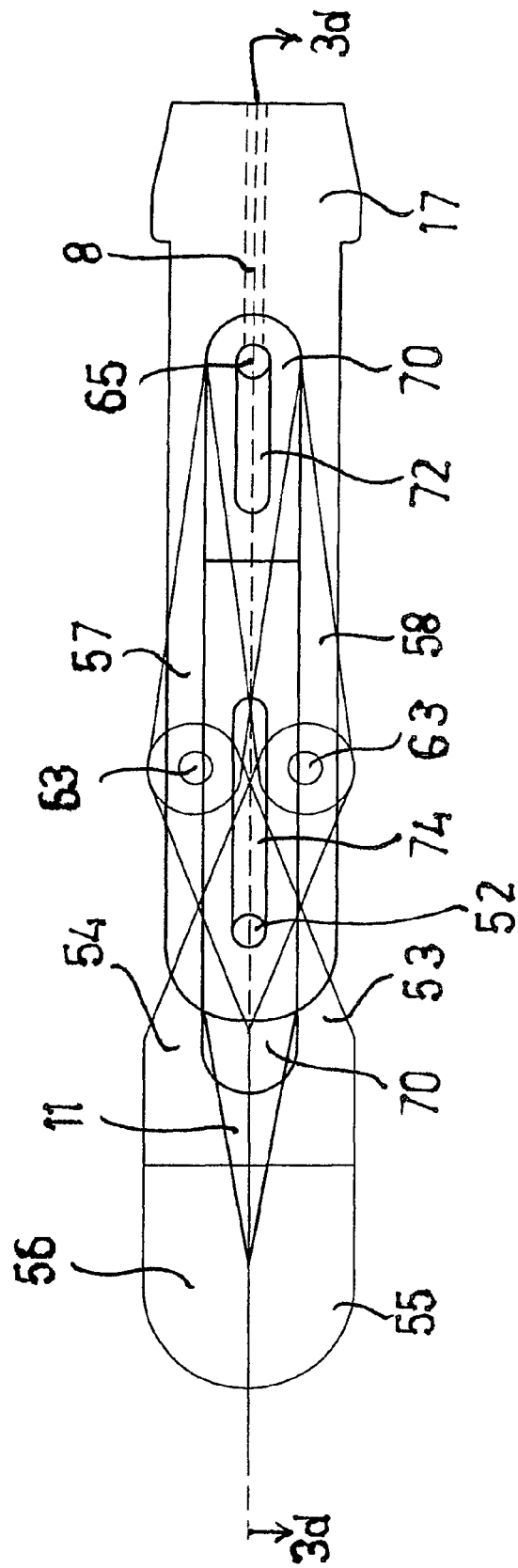
FIG. 3a is a partial sectional sideview of the distal portion of the forceps of FIG. 2, in a closed position.
Figure 3D:
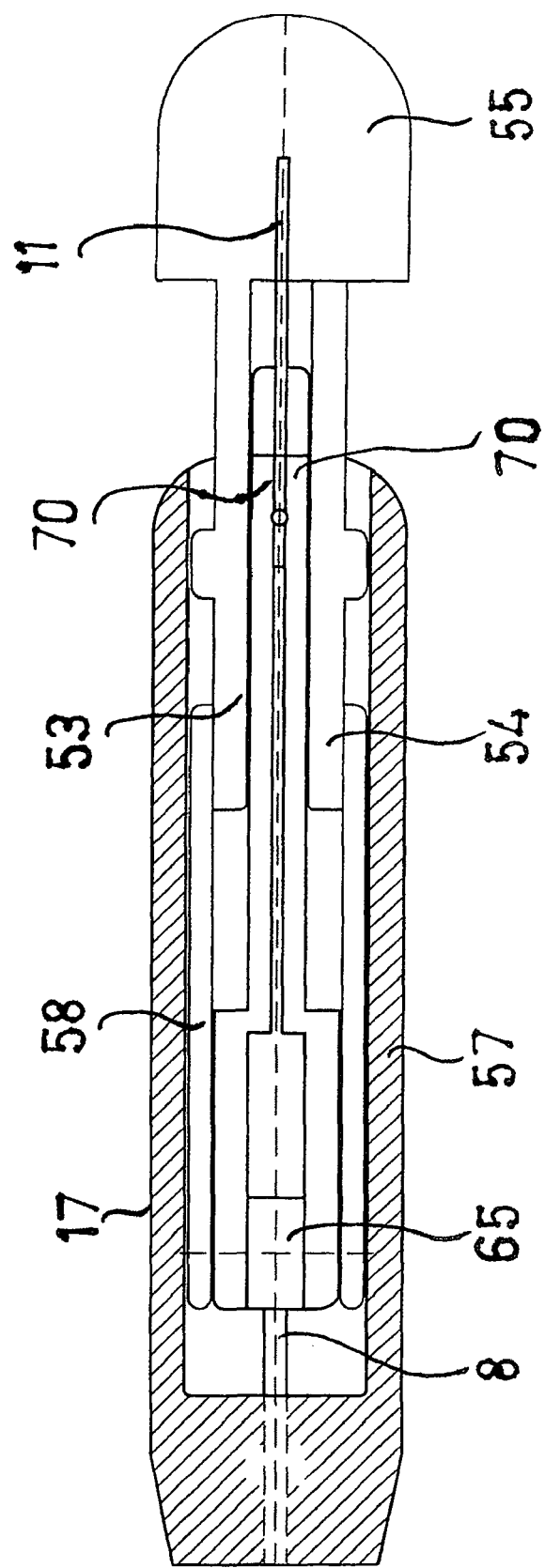
Figure 3E:
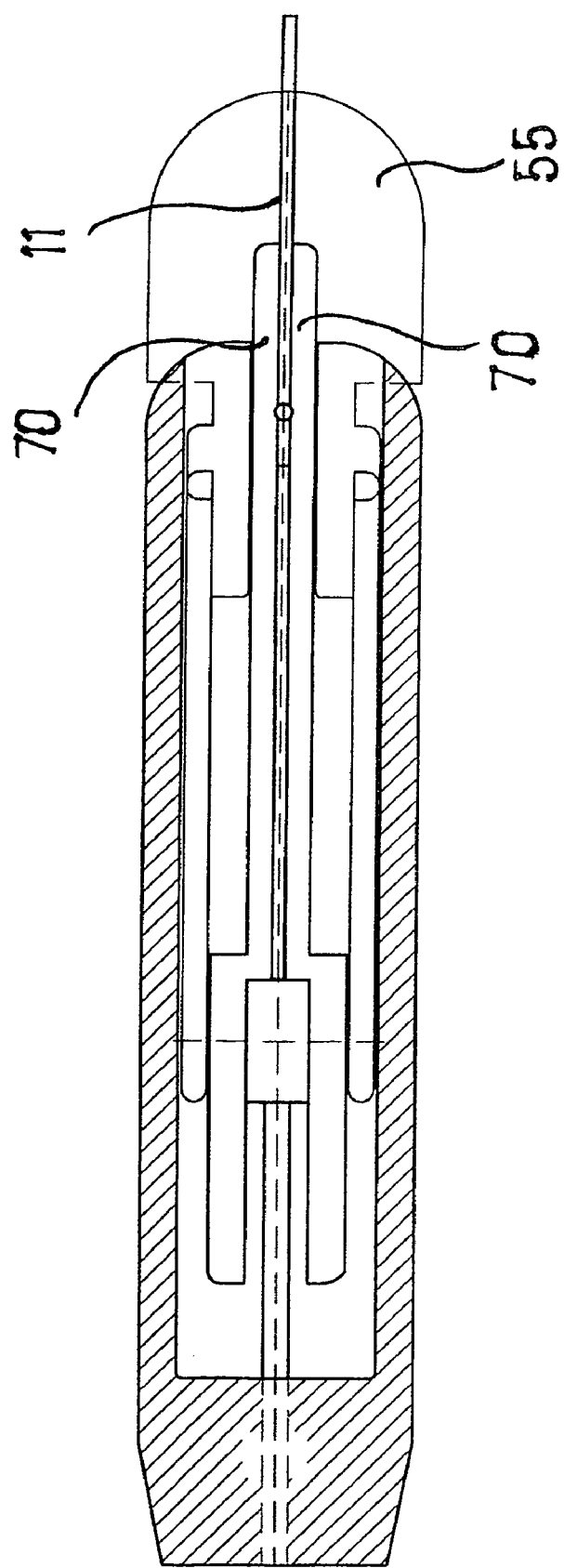
FIG. 3e is a cross-sectional view taken along line 3e-3e of FIG. 3b.
Figure 3F:
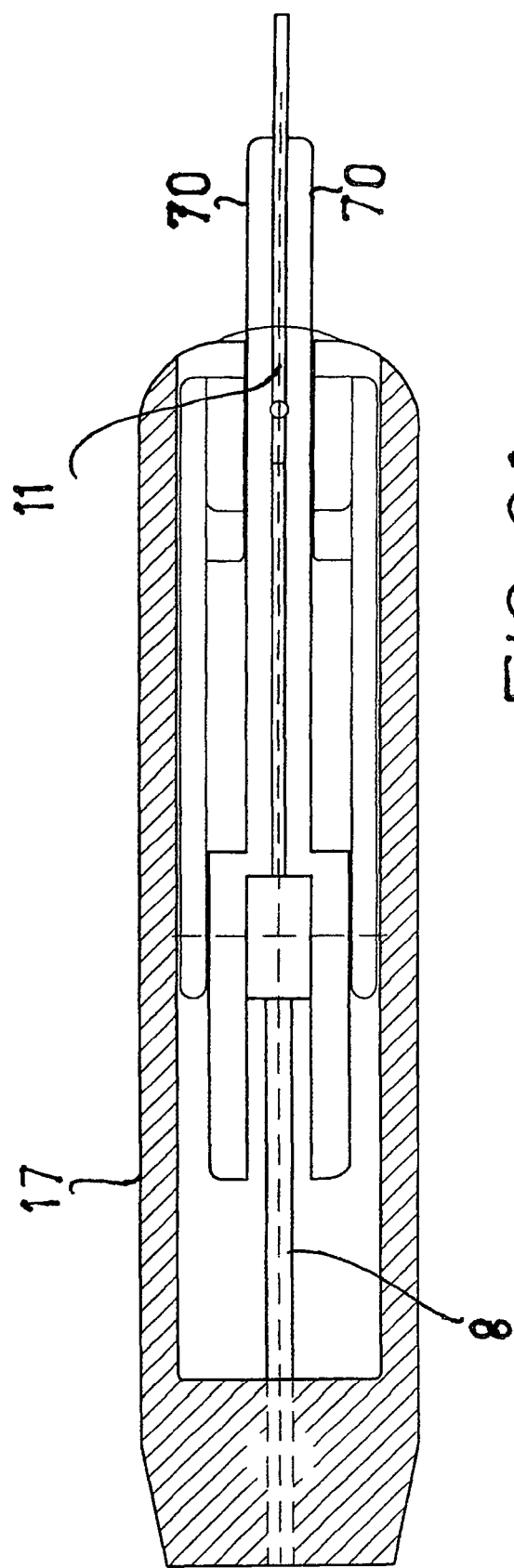
FIG. 3f is a cross-sectional view taken along line 3f-3f of FIG. 3c.
Figure 6A:
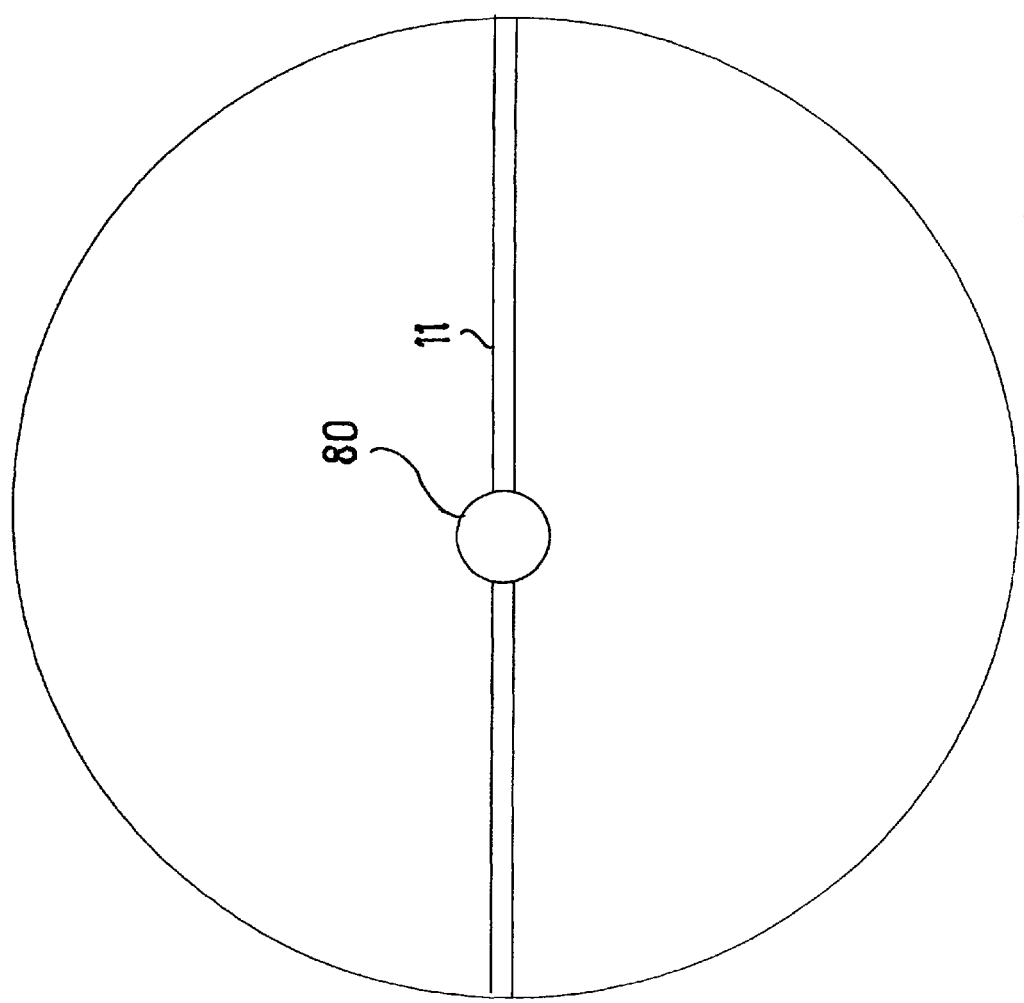
Figure 6B:
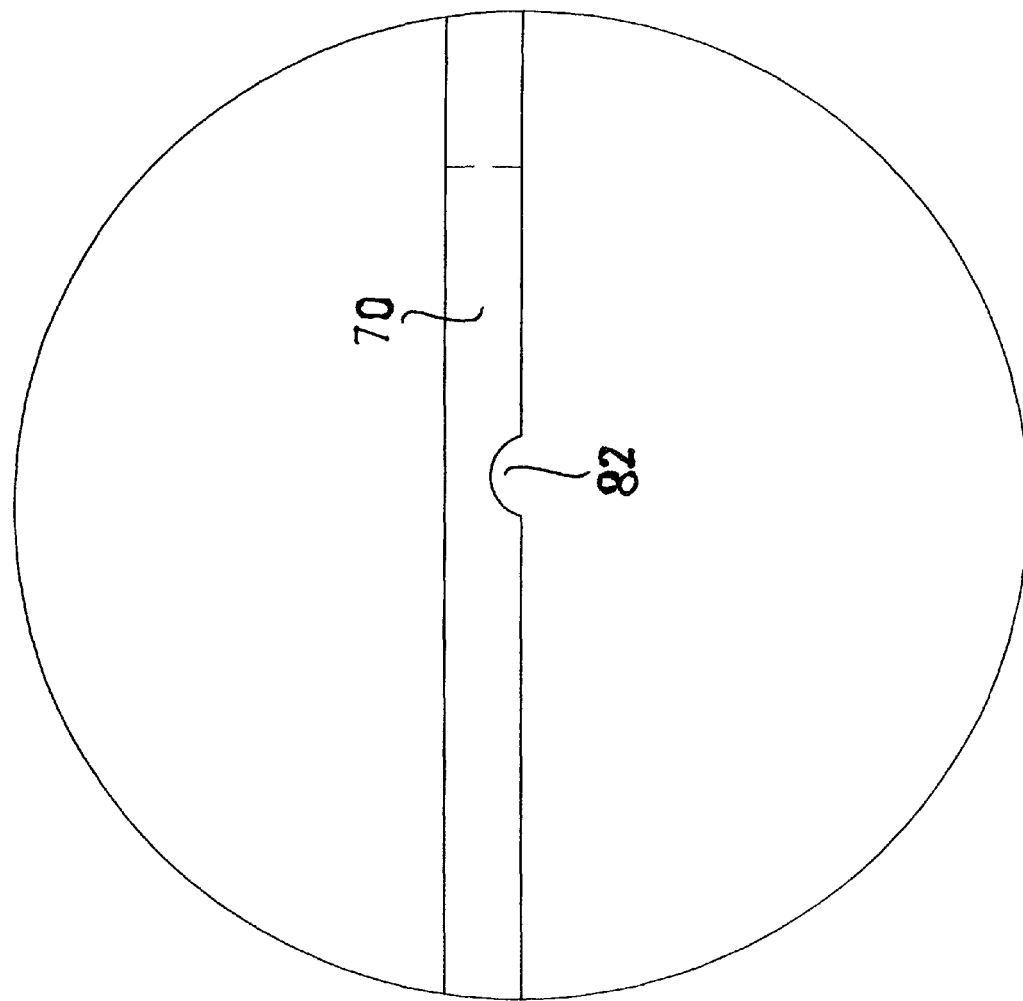
FIG. 6b is an enlarged side elevation view of the sliding plate member shown in FIGS. 4 and 5.

The spatial relationship of the elements is fully shown in FIGS. 3d, 3e and 3f which are sectional views taken along section line V-V of the clevis 17 and cable 5 in FIGS. 3a, 3b and 3c. Levers 57 and 58 are offset from the axial centerline of cups 55 and 56. In this embodiment scissor linkages or arms 53 and 54 are positioned between levers 57 and 58 and cups 55 and 56, respectively, and pivot about pins 63. Other arrangements will be apparent to those skilled in the art for producing the required movement of the sliding plates 70 from their proximal to distal position when the cups 55 and 56 are moved to the fully opened position for relative movement of the needle and contacting surface to discharge the tissue sample A mechanical or electro-mechanical retraction means can be utilized to move the needle relative to the sample contacting surface. A biasing spring, or a hydraulic or pneumatic pressure device can provide the force to produce the relative movement. The biasing spring can be operated in the compression or the expansion mode, the device preferably being brought into an "armed" or biased position prior to use of the apparatus, and most preferably, before the forceps are placed in the working channel or tube of the endoscope. This construction and mode of operation enables the practitioner to prepare the forceps and check its operational characteristics even before the procedure is initiated on the patient. It also minimizes the number of manual steps that must be performed to deposit the typically small biopsy tissue samples into the sample receiving container.

Other alternatives for controlling the reciprocating movement of axial rod 40 and distal needle 11 include hydraulic and or pneumatic cylinders or pistons. Small pumps and/or pressure tanks can be utilized to provide the pressurized fluid. Such devices are in common and long-standing use, and disclosures of suitable pneumatic systems are to be found in the prior art.

Another preferred embodiment of the invention is illustrated in FIG. 8 where the proximal end of the forceps includes body 90 and projecting finger grips 92 and thumb piece 23. As best shown in FIG. 9, this embodiment includes a needle 11 that passes through moving by-pass members 94 located at pivot positions 52 and 65 described above at FIGS. 2 and 3A. A needle channel 96 slidingly receives needle 11, in members 94 which at its proximal end is attached to wire 8 by an appropriate friction or mechanical attachment fitting 98.

When the needle 11 is withdrawn proximally, the face of distal by-pass member 94 and adjacent scissor arms 53 and 54 form a sample contacting pusher surface that slides longitudinally relative to the needle during a specimen ejection procedure and the sample S is displaced down the needle to be dislodged at its distal end.

Figure 10A:
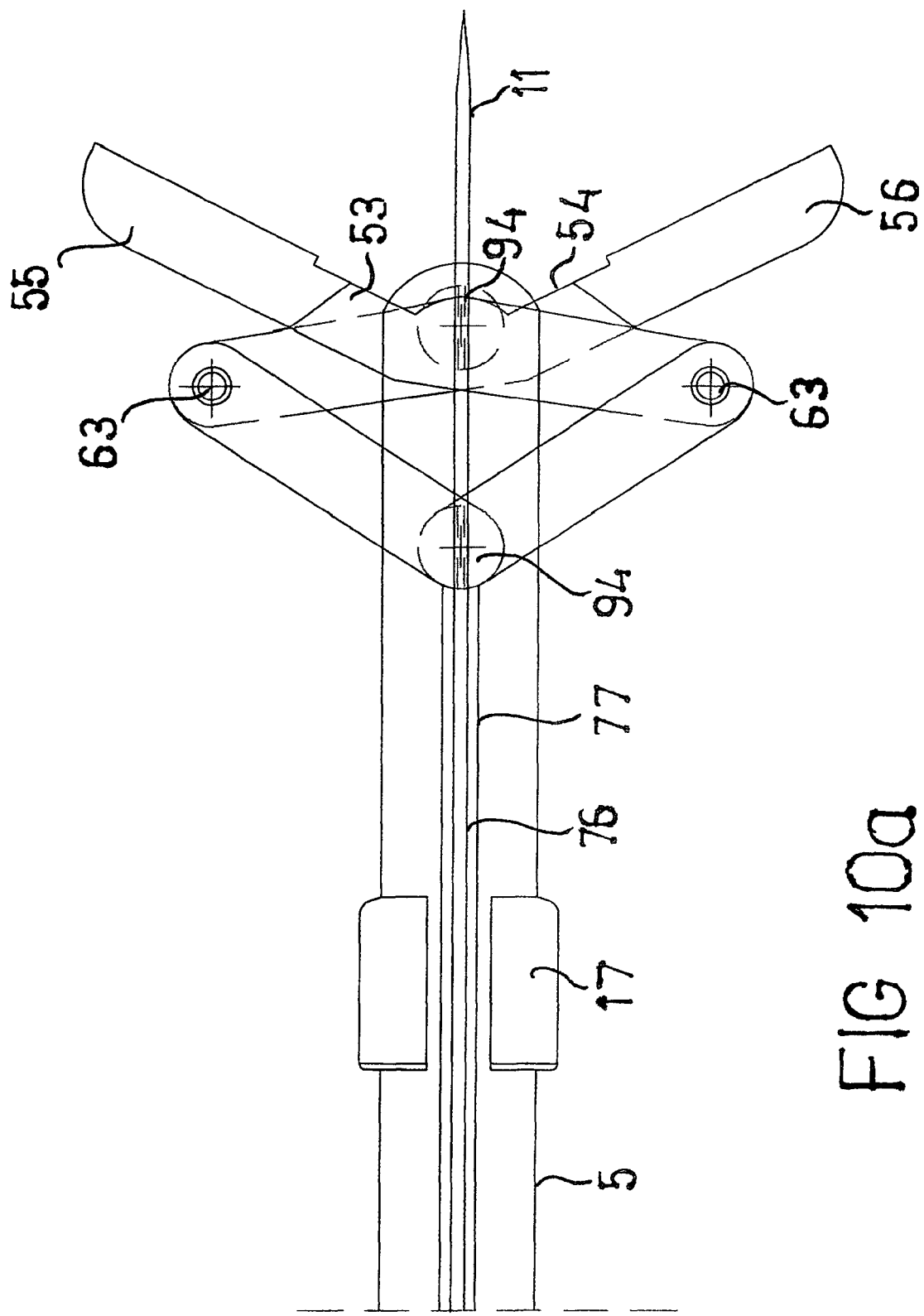
FIG. 10a is a partial sectional view of the distal portion of the forceps of FIG. 8 in a fully open position and ready for use.
Figure 10C:
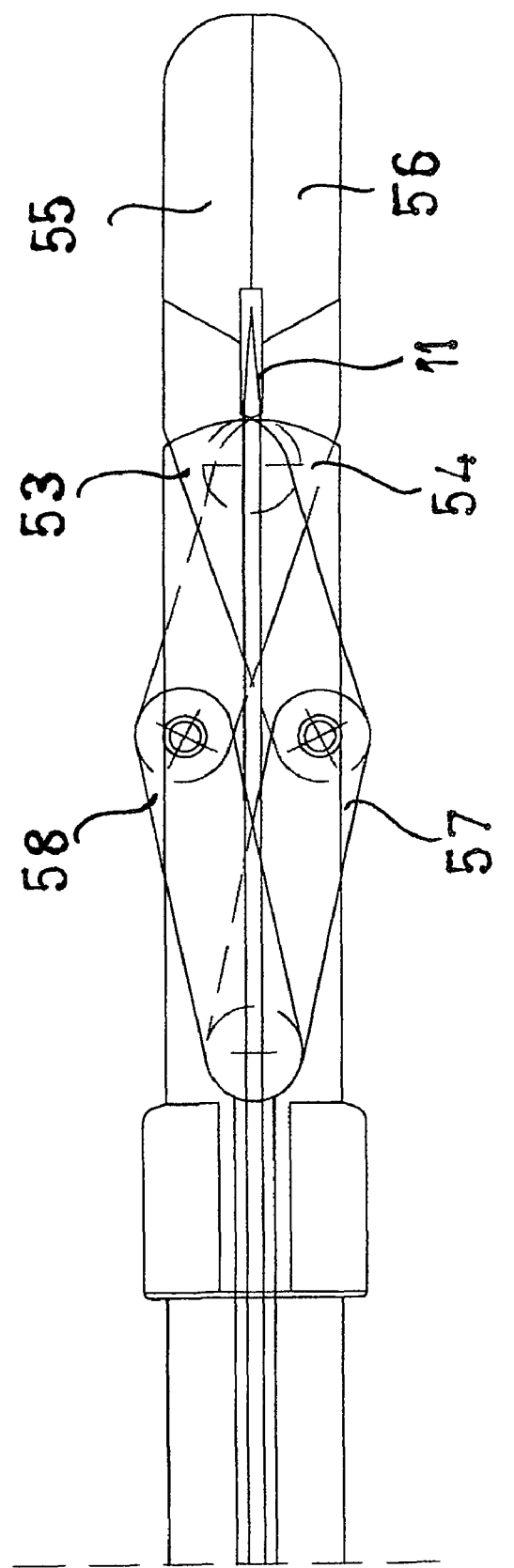
FIG. 10c is a view similar to FIG. 10a with the needle fully withdrawn from the cups.

In a further embodiment of the invention illustrated in FIGS. 10*a*, 10*b* and 10*c*, the needle 11 is mounted for reciprocal movement in response to the movement of thumb ring 23. As shown in the series of section views of FIGS. 10*a*, 10*b* and 10*c*, the first wire terminates in a hollow tube 77 that is operably attached to the proximal end of scissor links to open and close cups 55, 56. The use of hollow tube 77 permits rod 76 to freely slide in response to second wire 8 operably attached to thumb ring 23, to thereby advance and retract needle. As needle 11 is withdrawn proximally, any tissue sample mounted thereon will be engaged by the sample contacting surface formed by the leading edges of open arms 53, 54 and centrally disposed distal guide member 94. Other arrangements of the elements can be selected by one of ordinary skill in the art to effect the same resulting relative movement. For example, member 94 can be disposed adjacent the outside surface of one of the cup supporting arms 53, 54. The functional relationship of rod 76 and tube 77 can also be reversed, and other obvious mechanical equivalents can be substituted in their place.

Figure 11:
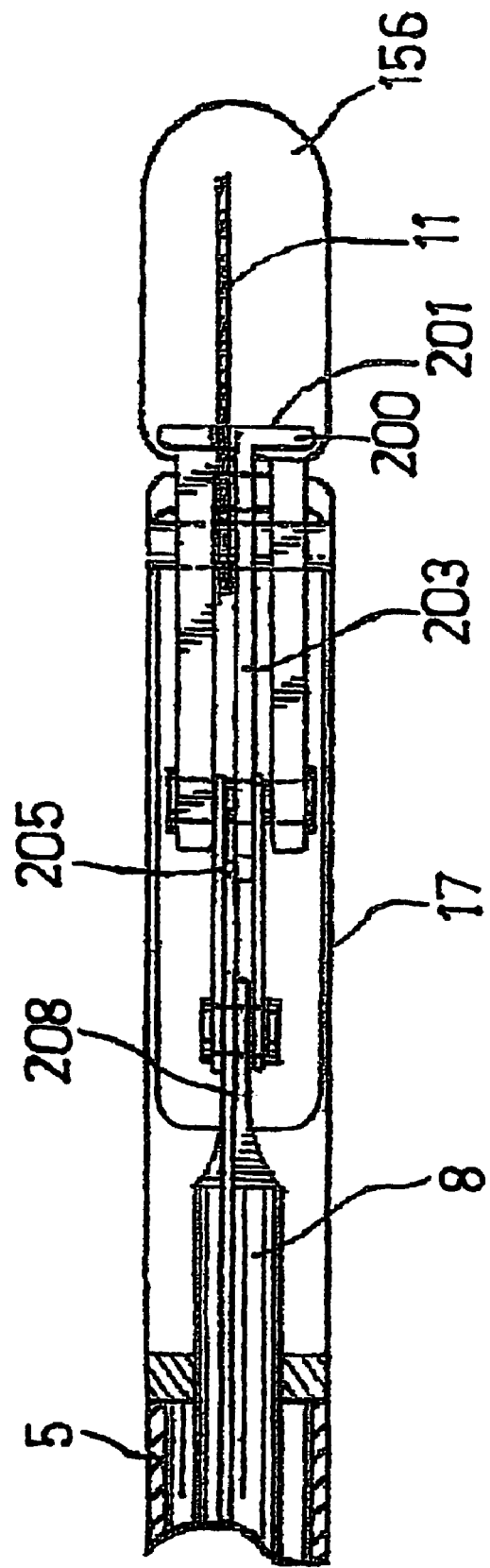
FIG. 11 is a plan view in partial section of the distal end of a biopsy forceps illustrating another embodiment of the invention in a closed position.
Figure 12A:
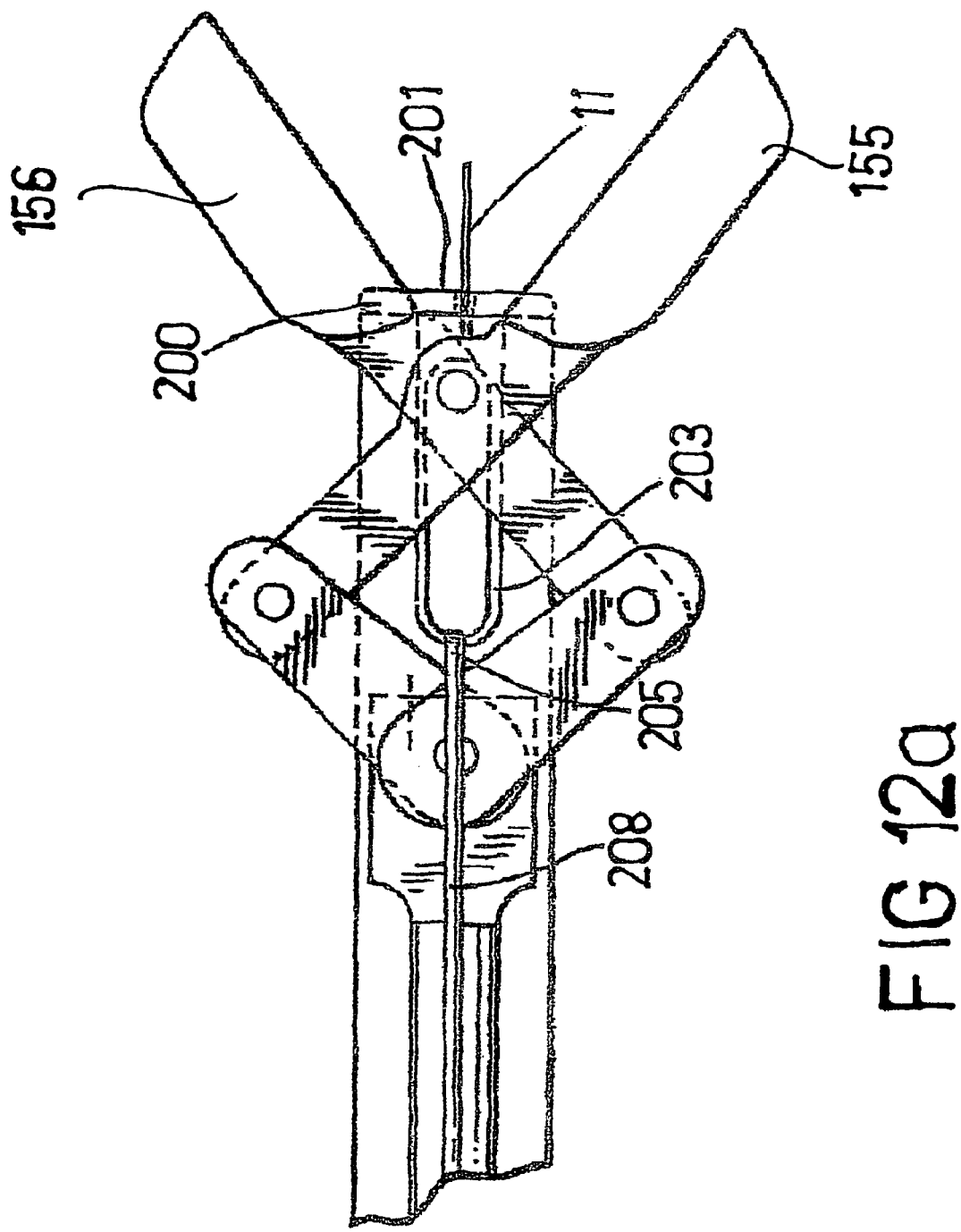
FIG. 12a is a side view in partial section of the device of FIG. 11 in an open position.
Figure 12B:
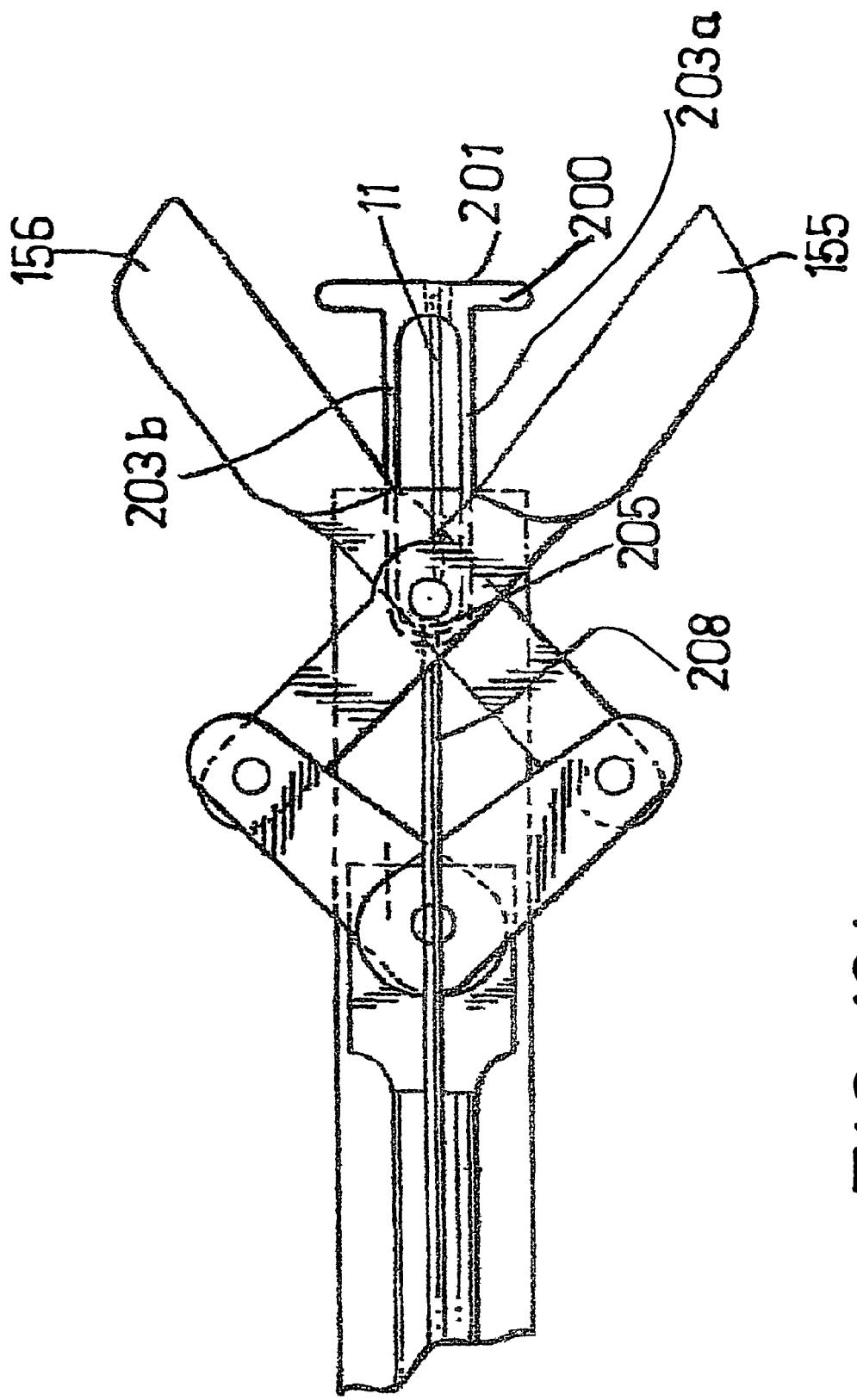
FIG. 12b is the same view as FIG. 12a in which the ejection means is extended.

A further embodiment of the invention is shown in FIGS. 11, 12*a* and 12*b*. In this embodiment, an ejector plate assembly 200 is attached to the distal end of a second wire 208 which is carried in flexible cable 5 adjacent and parallel to wire 8. As shown in FIGS. 12*a* and 12*b*, the ejection plate 200 is generally T-shaped in cross section and comprises a generally circular or oval top sample contacting surface 201 that fits closely within the proximal end of the cups 155, 156 when they are in the closed position. Joined to, or formed integrally with the underside of contacting surface 201 is leg member 203, which in this embodiment is comprised of a pair of spaced-apart elements 203*a* and 203*b*, joined at their proximal ends.

Wire 208 is secured to the proximal end of leg 203 at 205. The proximal end of wire 208 is secured to manual actuator means at the proximal end of the flexible cable 5. The ejection plate actuator means can comprise a separate finger or thumb grip having the configuration of thumb grip 23 shown in FIG. 2. Alternatively, wire 208 can be slidably affixed to spool 20 so that wire 208 is advanced in the distal direction only after the cups 155 and 156 have been fully opened and the release mechanism 91 has been activated.

The wire 208 with the ejection plate 201 and hole 200 can be used in conjunction with the prior art mechanism described in connection with FIG. 1 for opening and closing the cups 155 and 156. A distal movement of the wire 208 moves the plate 201 in a distal direction, as shown in FIGS. 12*a* and 12*b*. A tissue sample on the needle 11 is moved distally by the plate contacting surface 201.

Figure 13:
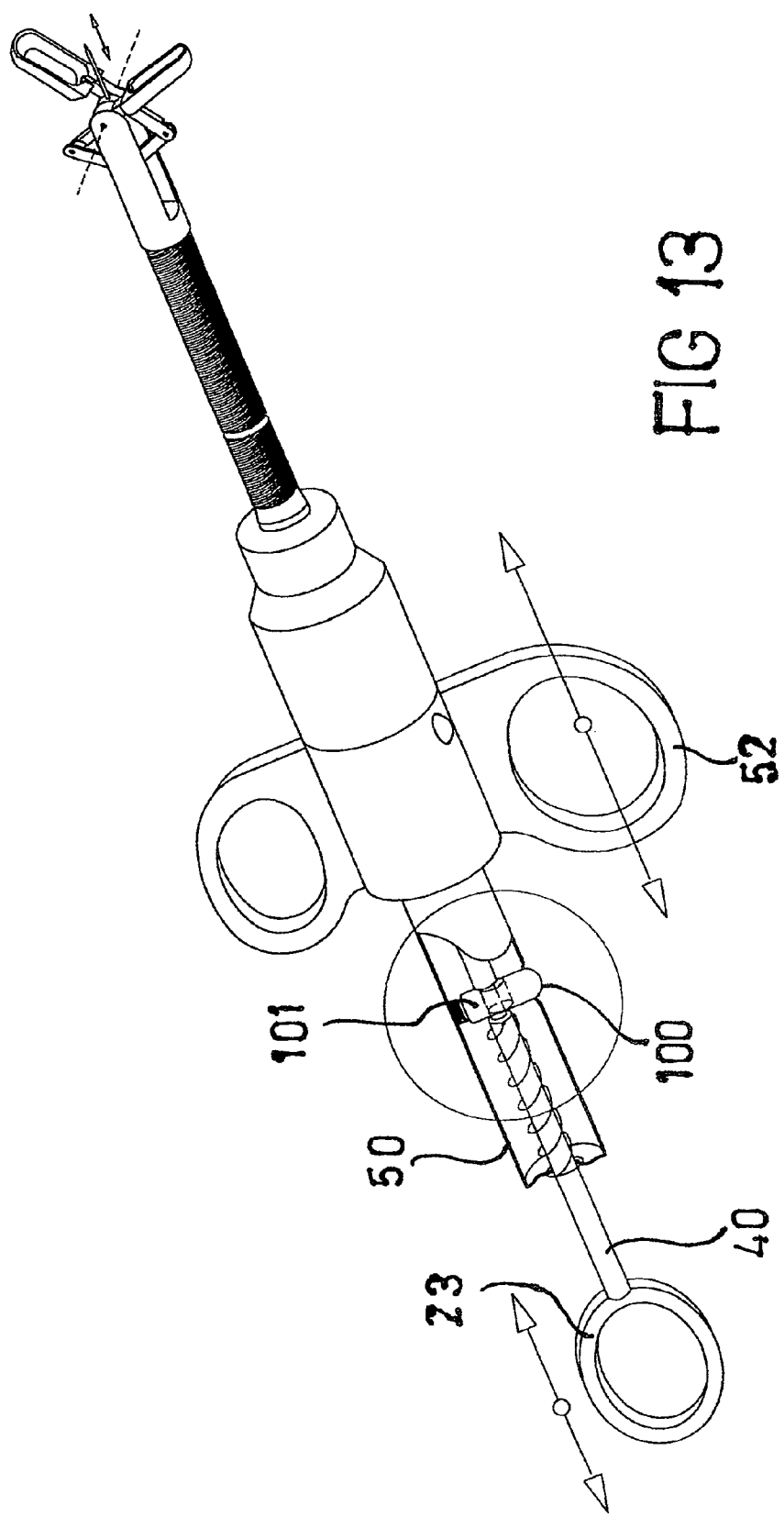
FIG. 13 is a front and side perspective view in partial section of the forceps of FIG. 8 illustrating one embodiment of a biased release mechanism.
Figure 14:
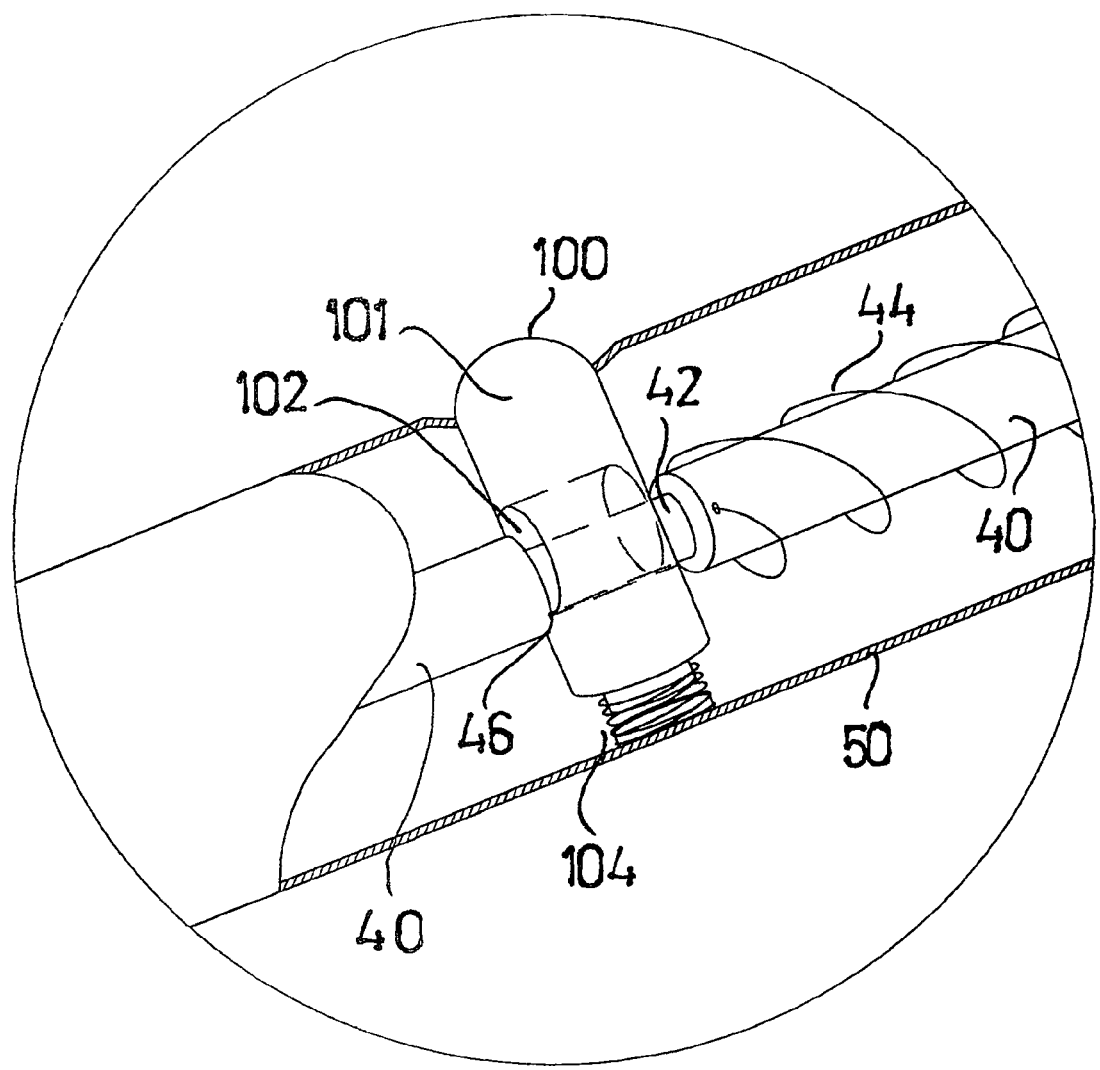
FIG. 14 is a detail of the mechanism shown in FIG. 13.

With reference to FIGS. 13 and 14, one preferred embodiment is illustrated of a mechanical spring-biased needle-retracting apparatus that functions in response to a push-button 100 located on the barrel 50 at the rear portion of handle assembly 20. Referring to FIG. 13 and the enlarged portion A shown in FIG. 14, axial rod 40 is provided with a slot or grooved portion 42 of a smaller diameter which passes through channel 102 in the depending shaft 101 of push-button 100. Push-button biasing spring 104 urges the lower portion of the shaft 101 against shoulder 46 of rod 40. The opposing ends of rod biasing spring 44 are secured to rod 40 and to housing 50, so that when the components are in the armed position illustrated in FIG. 13, spring 44 is in extension. When a force F is applied to depress button 100, the rod 40 moves toward the proximal end of the forceps, thereby withdrawing the needle and dislodging any tissue sample(s) positioned on the needles.

As will be apparent to one of ordinary skill in the art, the biasing spring can be mounted for compression in the armed state on the opposite side of groove 42. The compression spring can itself be mounted in a groove in rod 40 and retained by a collet or other mechanical fastener Before inserting the biopsy forceps into the working channel of the endoscope, the needle is locked into place by pushing the thumb ring distally. This action expands the spring 44 inside the handle 5 and the spring-biased pushbutton 100 snaps into place. The forceps are then inserted into the endoscope working channel.

When the device is inside the body, the cups are opened to the working position by pushing the handle finger rings 52 (FIG. 13) distally with the index and middle fingers. The pusher rod 76 (FIG. 10A) is connected to the moving needle by-pass piece 94 (FIG. 10A). It is hollow and contains the needle 11. The needle, which is still in the fixed position, receives the biopsy tissue. After obtaining one or more biopsy samples, the forceps is removed from the endoscope working channel in order to place the biopsies into a container with a preservative solution, e.g., formalin.

The cups are opened to the working position and the spring-biased push button 100 is depressed. The spring contracts causing the needle 11 to retract proximally into the body of the forceps, and the samples contact the pushing means thereby ejecting the biopsy samples into the formalin container.

Figure 15B:
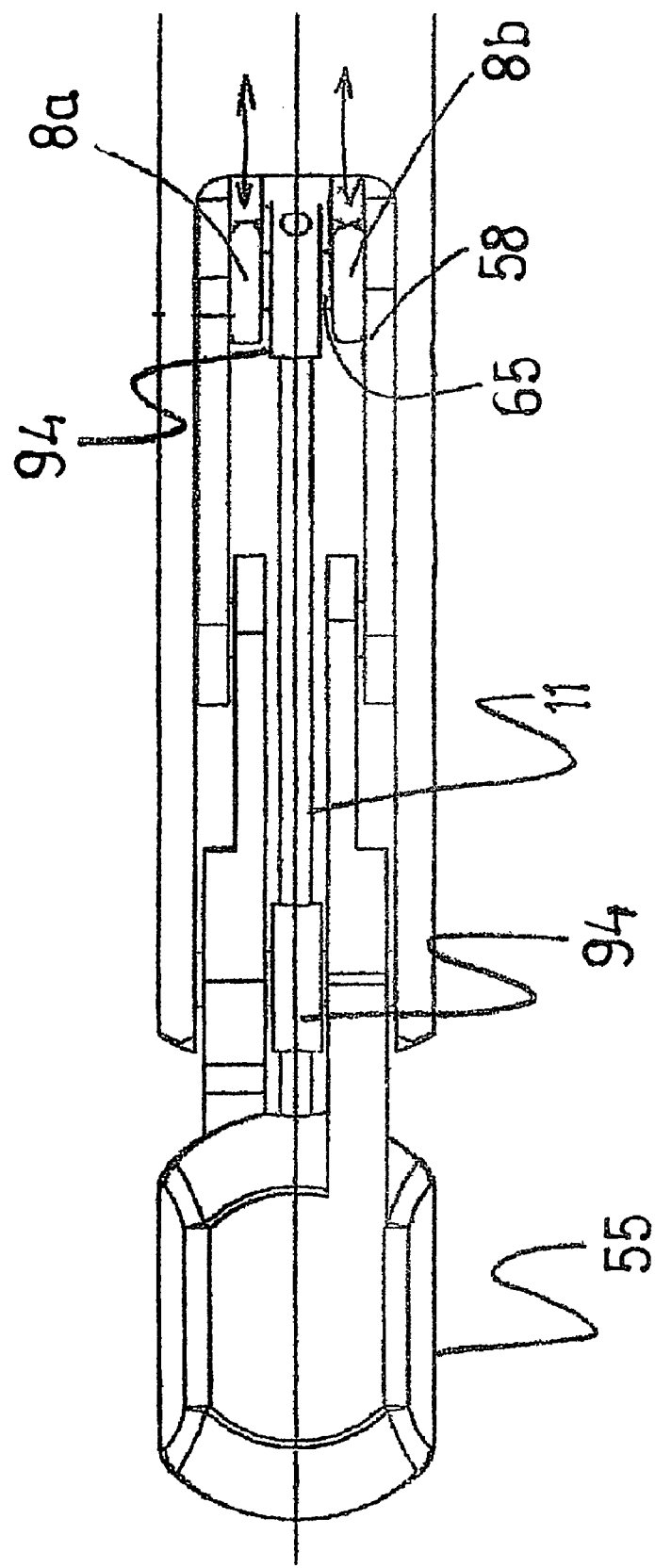
FIG. 15B is a partial top plan view of the embodiment of FIG. 15A taken along line 15B-15B.

A further embodiment of the invention is illustrated in FIGS. 15A and 15B, where the proximal ends of the scissor links 57 and 58 are pivotally mounted on the proximal bypass element 94 through which needle 11 passes in a sliding relation. A pair of wires 8A, 8B extend from a movable control handle at the proximal end of the instrument, such as handle 92 in FIG. 8. The respective distal ends of wires 8A, 8B are secured to transverse pivot pin 65 to which are attached scissor arms 57 and 58. As best shown in the partial top view of FIG. 15B, the distal movement of wires 8A, 8B causes pivot pin 65 to move in the corresponding direction and to move the scissor mechanism to open opposing cups 55 and 56, thereby exposing needle 11 and permitting the sample to be engaged.

When the wires are moved proximally, cups 55 and 56 close around the tissue and sever the sample from the organ, leaving the samples on the needle shaft. This particular two-wire construction provides a direct positive control over the movement of the scissor mechanism and has the effect of providing dual activation means. As will be apparent to one of ordinary skill in the art, the use of a pair of parallel wires 8A, 8B also serves to enhance the reliability and operability of the biopsy instrument, since the scissor mechanism can be made to function normally, even if only one of the wires remains attached at its distal end to pin 65 and its proximal end to the sliding handle. As will also be apparent, other control means, such as a wire cable or flexible but non-extensible member can be utilized.

Before inserting the device into the working channel of the endoscope it is necessary to lock the movable needle in place. This is accomplished by moving the thumb ring distally to compress a spring located in the handle portion. The button 100 is displaced to allow for the thumb ring travel and then snaps into place after complete extension of the needle to which it is connected. If a support tube is used to facilitate movement within the cable, it moves with the wire as it is extended. The wire, and the support tube (if used) can be secured to the thumb ring by any conventional means, e.g., adhesive.

The cups are operated by moving the slider 90 distally to open and proximally to close. This is accomplished through the use of two (2) drive wires each surrounded by a support tube. The support tubes move with the drive wires during actuation. The drive wires can be attached to the slider by the use of wire pins of the same material as the slider which are press fit into the slider and pinch the drive wires into place. This connection must be accomplished during final assembly to ensure that the proper tension and tolerances are achieved for opening and closing the cups.

In addition to the holes for the mating wire pins, the slider has a slotted opening for tensioning of the wires with a small hand tool before they are secured in place. This access slot also allows for positioning and securing the movable needle wire into the thumb ring. The wires are tensioned in place as the wire pins are inserted securely into the slider.

The button assembly is retained in an opening in the thumb ring 23 that permits their relative movement while also maintaining the thumb ring and preventing its removal from the handle. The button includes an integrally formed cantilevered spring and is locked against the handle. The user can easily depress the exposed portion of the push button and release the assembly to retract the needle into the body.

Once the improved safety biopsy forceps of the invention have been positioned inside the subject's organ, the cups are opened to the working position by pushing the slider distally. The drive wires are connected at the distal end to the proximal needle by-pass member 94 which is free to move in a linear direction. The needle by-pass which is connected to the scissor links allow the movable needle to pass through while the cups are being moved between the open and closed positions. The needle by-pass is connected to the cups during actuation of the drive wires. The pivot of the cups is stationary and held in place by two (2) pins which secure the cups and a second distal needle by-pass member 94 securely in place.

The movable needle 11, which is still in the fixed position, receives the samples after which the instrument is removed from the working channel of the endoscope and positioned to place the samples into the container of preservative solution.

The cups are opened to expose the sample and the button 100 on the handle assembly 20 is pushed to retract the lower retaining portion of the movable needle. This is accomplished by disengaging the lower retaining portion 46 of the button 100 from the thumb ring shaft 40 and the expansion of the spring 44 which causes the needle to be retracted proximally into the body of the forceps and the biopsy specimens to be ejected into the preservative solution.

In a further preferred embodiment illustrated in FIG. 16, a hollow needle 300 is employed, the proximal end of which is in sealed fluid communication with a flexible conduit 302 terminating in female fitting 304 that has an internal orifice sized to receive a standard syringe 310. The syringe 310 is conveniently secured to the proximal portion of forceps body 90 by spring clamps 316 or other appropriate releasable fastener. The apparatus of this embodiment allows the physician to conveniently inject the tissue sample and/or surrounding anatomical area with any desired material, such as saline solution for elevating the mucosa and creating a safety cushion for the biopsy, a dye fluid that is radio-opaque, or a fluid that contains a radioactive tracer compound.

In the practice of the method utilizing this embodiment of the invention, the forceps are moved proximate the portion of the tissue to be injected, the cups are opened to expose the hollow needle 300 which is then advanced to penetrate the tissue. The physician then depresses conveniently located plunger 314 to eject the fluid from the barrel 312 of syringe 310. The fluid travels down tube 302 and from the hollow tip of the needle 300 into the tissue. Assuming that a tissue sample is also to be collected, then the cups are closed to surround and sever the sample while it is positioned securely on the needle 300.

As will be clear from the above description, a plurality of samples can be collected on needle 300. Depending upon the purpose of the biopsy, one or more of the plurality of tissue sample can also be injected with fluid from syringe 310.

Figure 17:
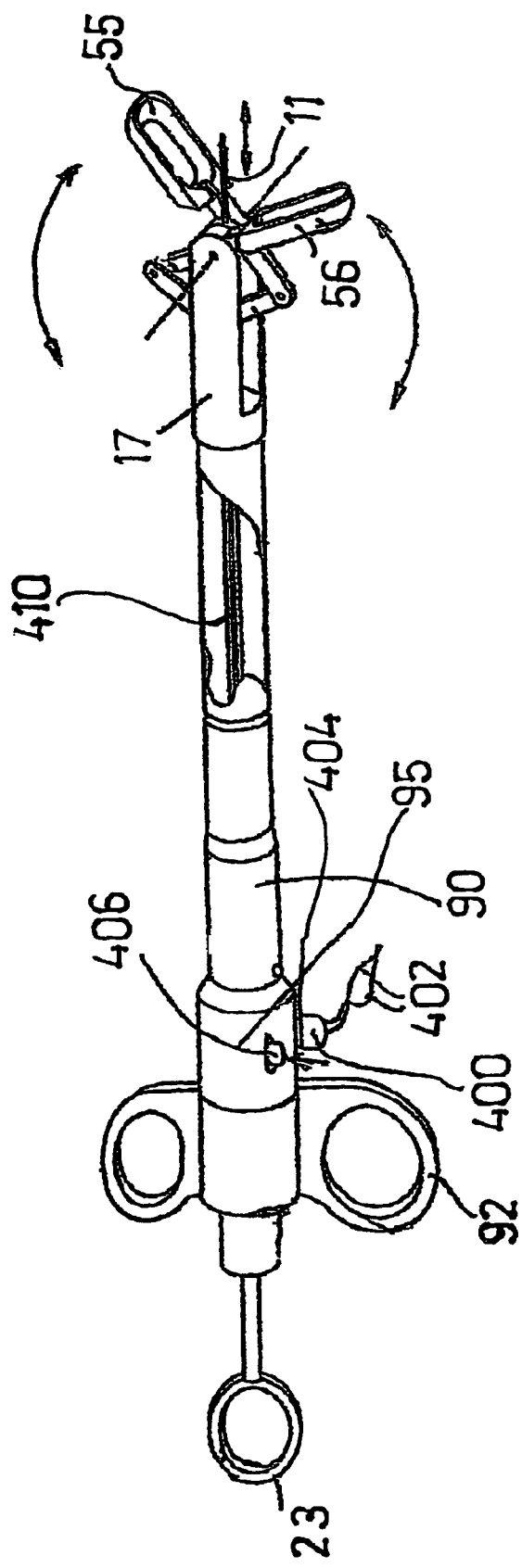
FIG. 17 is a perspective view of another embodiment of the invention having self-cauterization capability.

In the further preferred embodiment illustrated in FIG. 17, the needle biopsy forceps of the invention is provided with a cauterizing current that is provided by plug 400 with electrical conductors 402 leading to an appropriate power supply (not shown). An insulated socket 404 is fitted to forceps body 90 to matingly engage plug 400. Internal electrical conductors 410 extend through cable 5 from socket 404 to electrically conductive metal cups 55 and 56.

The needle 11 is isolated from the conductive cups 55 and 56, or is itself made from a non-conductive material, such as nylon, high density polyethylene or other suitable engineering polymer or copolymers. The needle 11 can also be insulated from the cauterizing current by the application of a conductive coating, e.g., a polytetrafluorocarbon sold under the trademark TEFLON® by the DuPont Company. The coating can be applied as a heat shrinkable web or by spraying. As will be understood by one of ordinary skill in the art, it is preferred to minimize the heat to which the recovered sample is subjected and the cups 55 and 56 can be made large enough to enclose, but not contact the severed tissue sample.

In the practice of the method of this embodiment of the invention, the cups 55 and 56 are opened and needle 11 is moved into position to penetrate the tissue to be sampled. The thumb and finger grips are moved to clamp the cups around the tissue on the needle and sever it. Simultaneously, the switch 406 is activated to send a brief cauterizing current through the cups 55 and 56 to thereby stop or minimize bleeding from the organ. The forceps can be advanced to collect additional samples or withdrawn for removal of the one or more samples harvested during the procedure in accordance with the description provided above.

Figure 21:
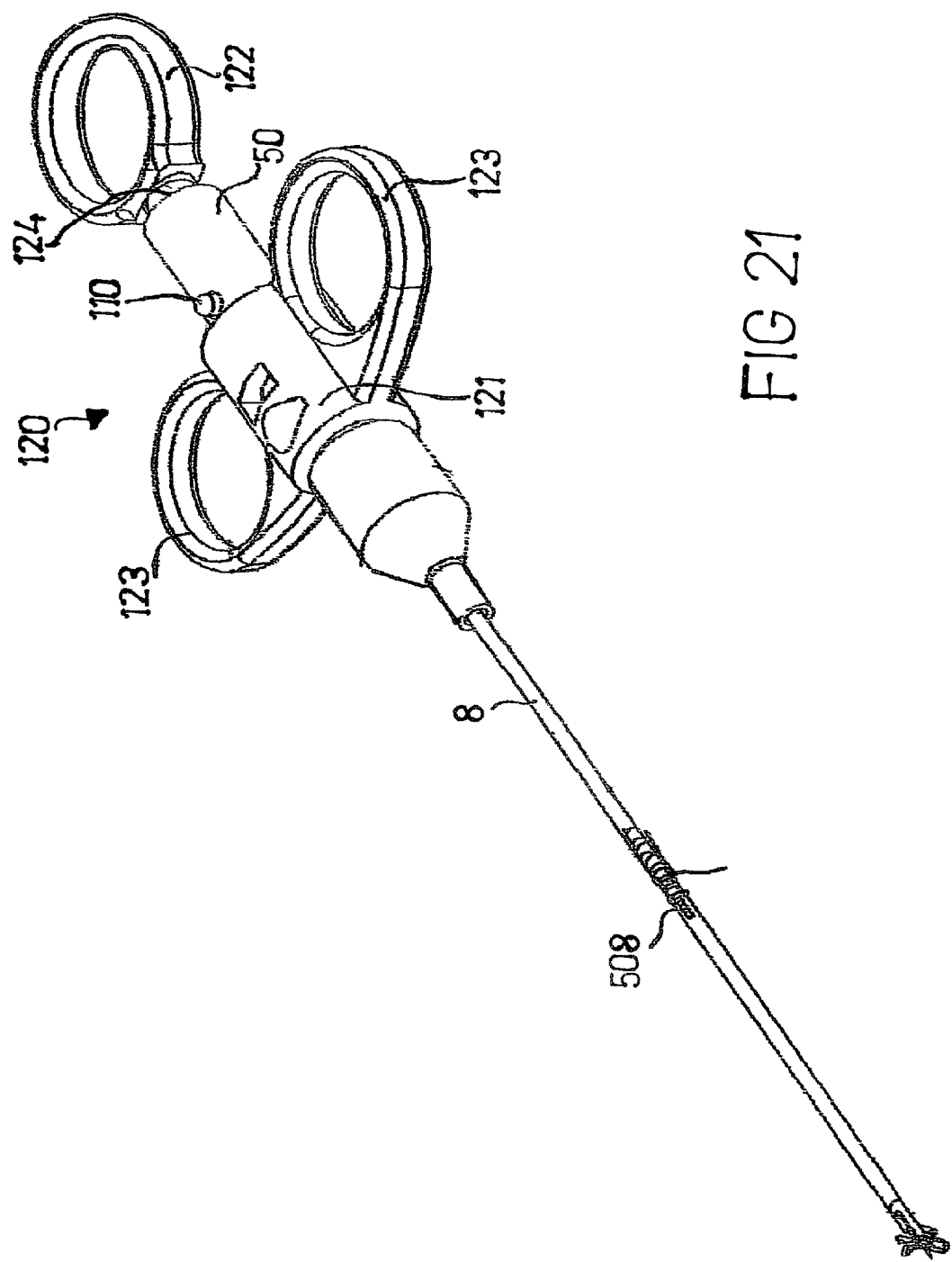
FIG. 21 is a perspective view of a further preferred embodiment of the invention illustrating the position of the forceps control and ejection means.
Figure 22:
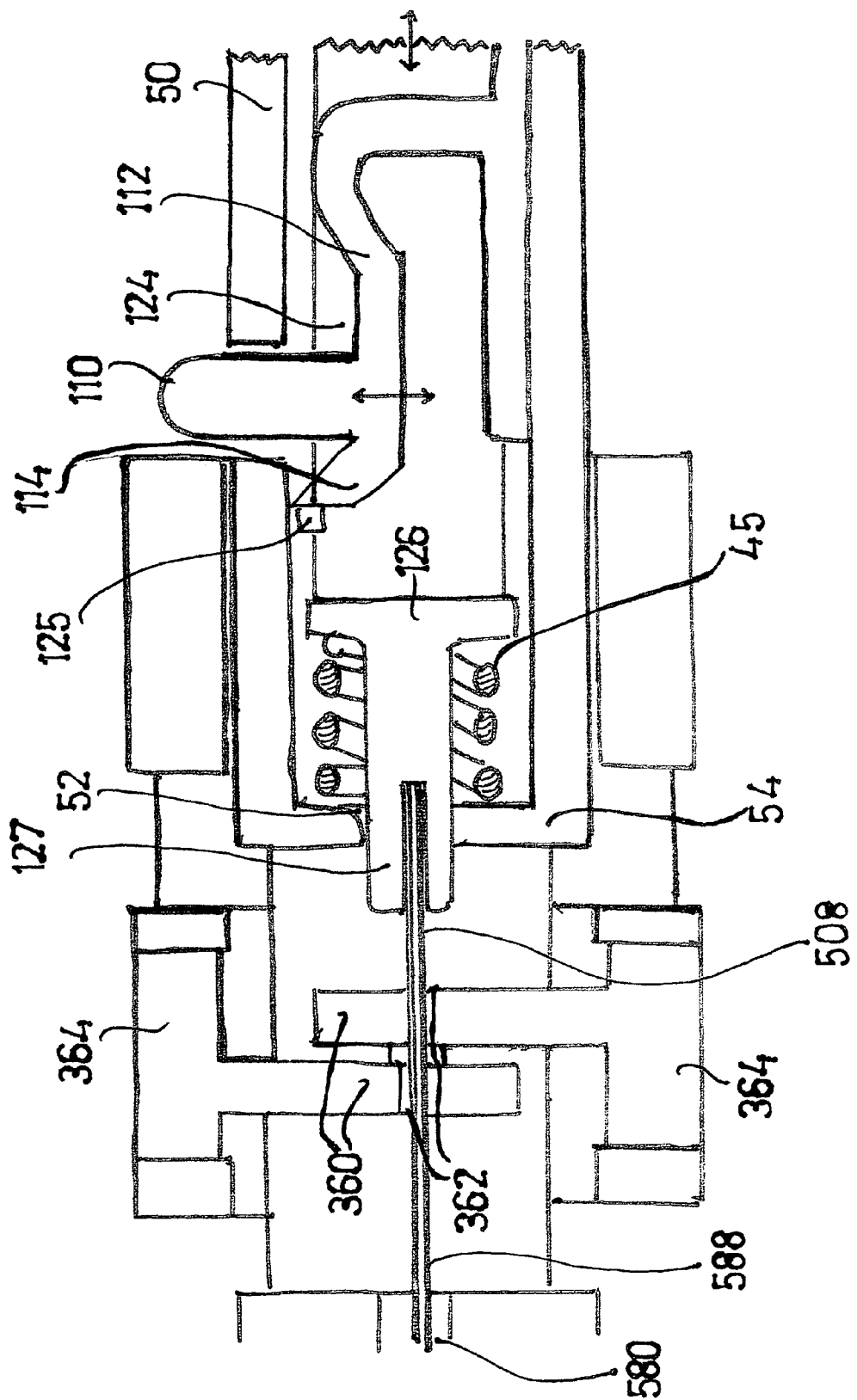
FIG. 22 is a cross-sectional side elevation view of a portion of the proximal end of the embodiment of the instrument of FIG. 18A schematically illustrating manual control and release members for enhancing the safety aspects of its method of use.

In addition to the control means illustrated and described in connection with FIGS. 13 and 14, another preferred embodiment of manual controls and releases positioned at the proximal handle end of the biopsy instrument are illustrated in FIGS. 21 and 22, below. As will be understood from the prior description, the invention has as one principal purpose and object, enhancing the safety of the medical personnel using it. By providing various control systems that are installed at the proximal handle portion of the instrument, personnel avoid the requirement of bringing their fingers into close proximity with the distal end where they might receive a puncture wound from the needle or a cut from the sharpened jaws of the cups.

Figure 18:
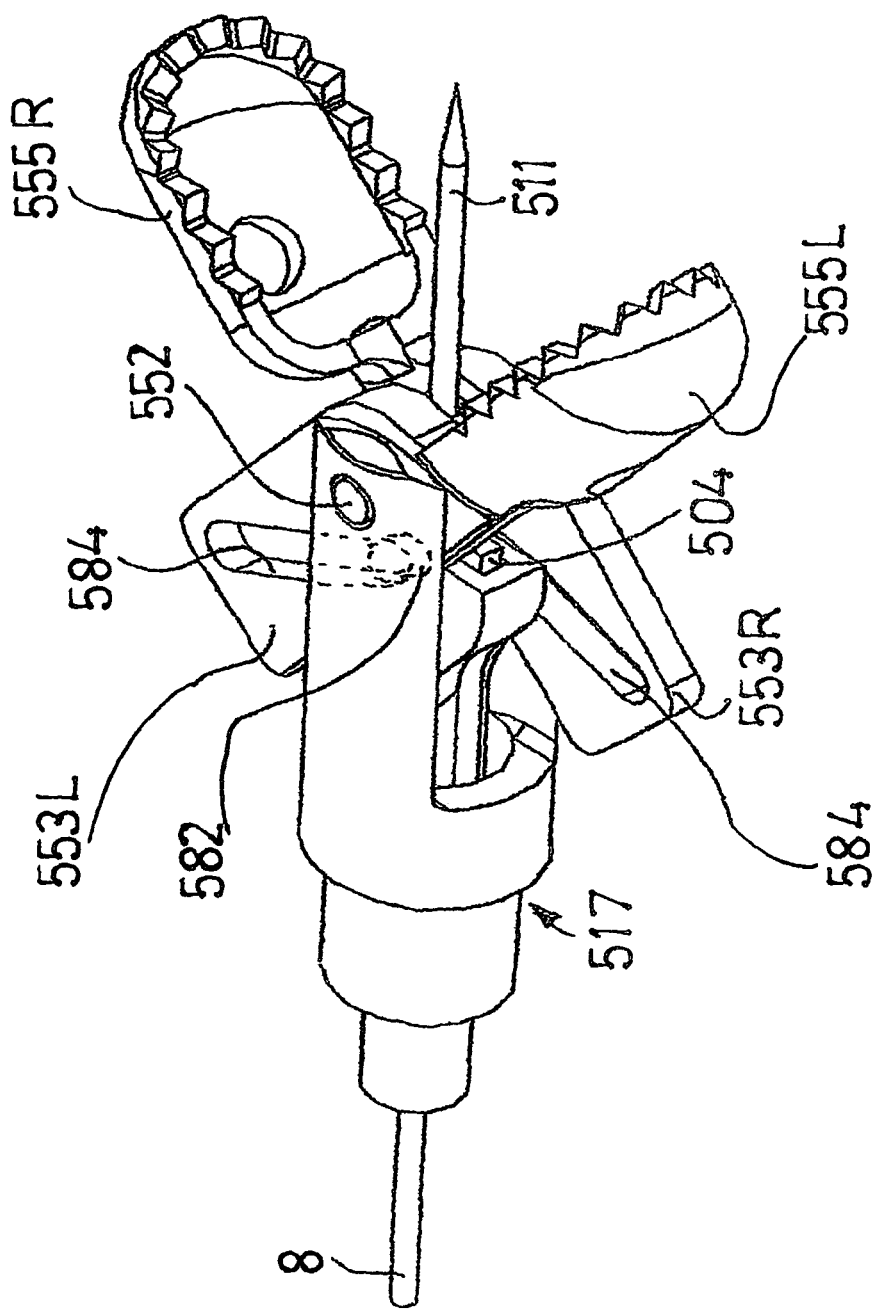
FIG. 18 is a top, front left side perspective view of another preferred embodiment of the invention.
Figure 19:
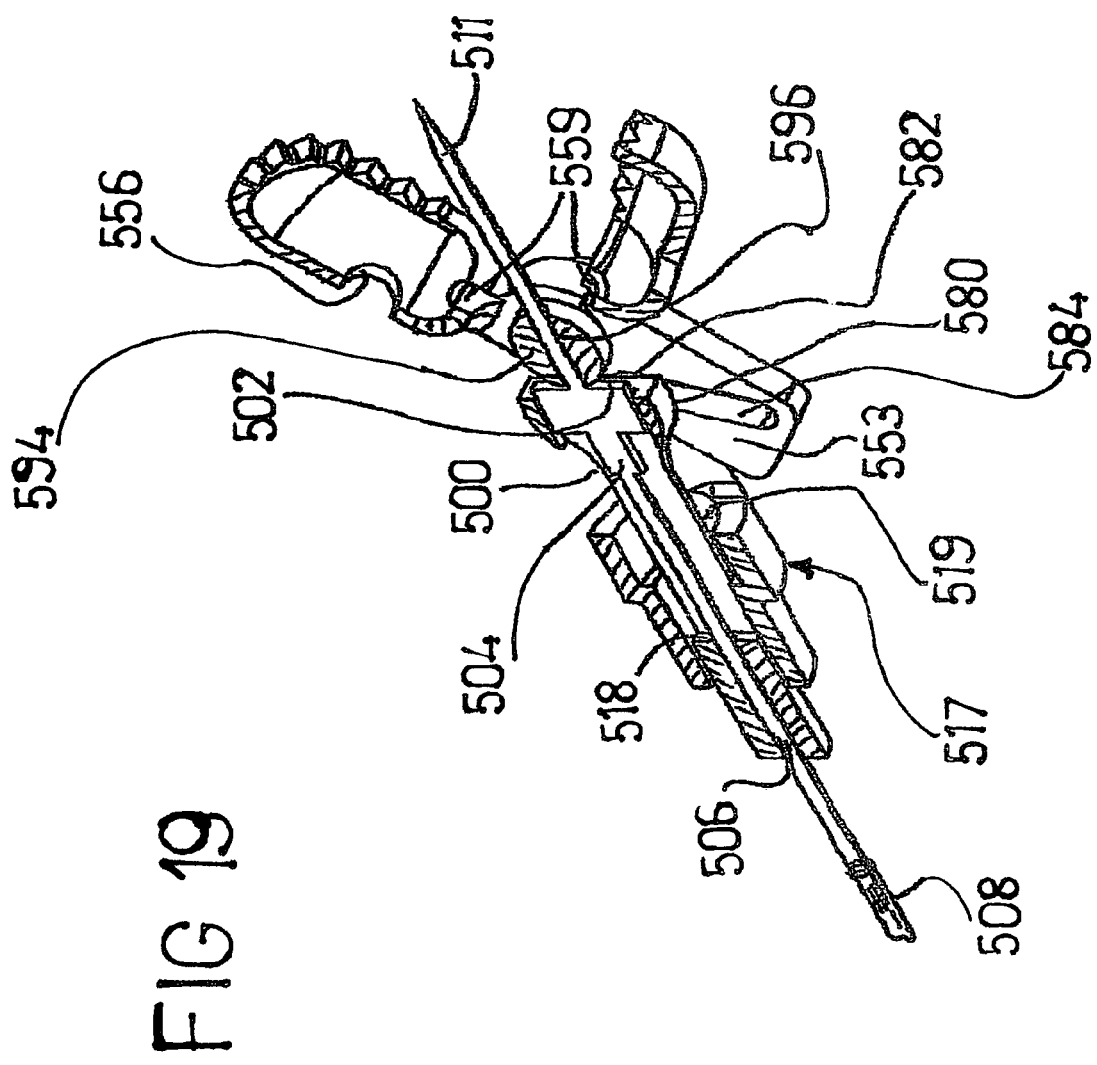
FIG. 19 is an elevation cross-section view of the embodiment of FIG. 18.
Figure 20:
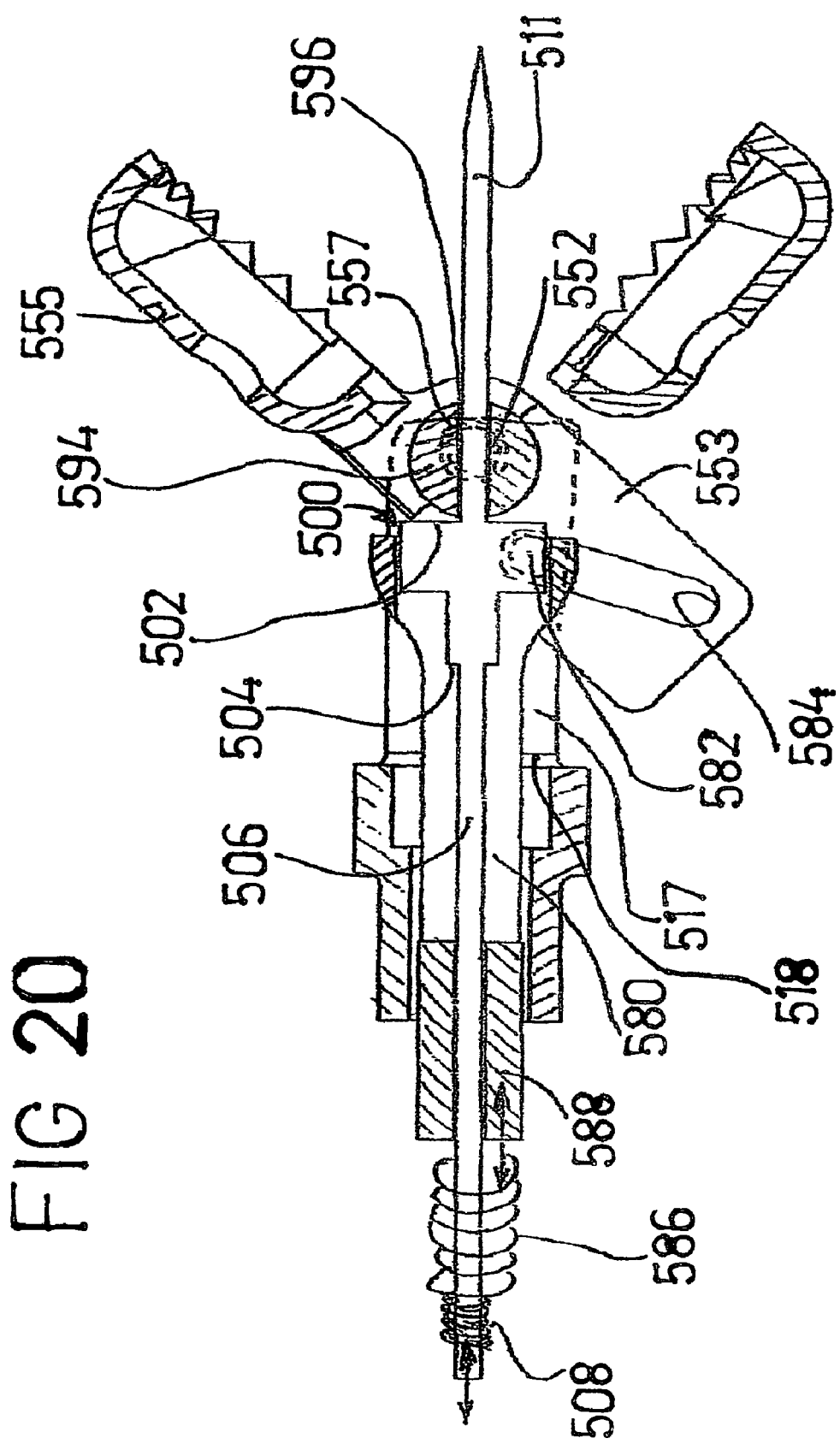
FIG. 20 is a side elevation view, partly in cross-section, of the embodiment of FIG. 18.

A further preferred embodiment is illustrated in FIGS. 18-20 in which a cam mechanism is employed to open and close the cups. In the embodiment illustrated, the needle 511 is integrally formed with a needle control assembly 500 that further includes a needle advance stop member 502 and a retraction stop member or surface 504 formed at predetermined distances from the sharpened needle tip, and a proximally extending tail piece 506 for attaching to the axial wire 508 that controls the movement of the needle portion 11. The needle control assembly 500 is preferably formed as one piece, as by stamping from a sheet material, machining or by molding from metal or polymeric materials that are well known in the art. This unitary construction of assembly 500 provides economy in manufacture and ease of assembly.

The distal end of the needle 511 passes through a central opening 596 in bypass member 594 that is preferably integrally formed with opposing transverse pivot posts 552 on which the cups 555R and 555L are pivotally mounted. The ends of pivot posts 552 are retained in corresponding openings 557 at the distal ends of the opposing arms of clevis 517.

As best shown in the cross-sectional view of FIG. 19, the clevis assembly 517 is formed with an axial opening 519 having an internal shoulder 518 for engaging the proximal surface of needle retraction stop 504 to limit the range of the movement of the needle 511. As also shown in FIG. 19, the axial channel 519 of the clevis extends proximally to receive the needle assembly tail piece 506.

As in prior embodiments, each of the cups 555 is provided with a groove 559 to permit passage of the shaft of needle 511. The cups can also be provided with at least one orifice 556 to permit the passage of fluid.

The opening and closing of the cups 555 is controlled by cam and follower means. A pair of cams in the form of fixed posts 582 extend transversely from a drive member 580 and contact cam follower surfaces 584 formed in the respective scissor-linked cup arms 553. The drive member 580 slides axially through the channel or axial passageway 519 in clevis 517. The cups are opened by moving the drive member 580 distally causing the cam follower surfaces 584 to move away from the axis of the instrument; moving the drive member 580 proximally brings the cup arms 553 toward the axis in response to the movement of the cam follower surfaces 584 against the proximal movement of cam post 582. As will be apparent to one of ordinary skill in the art, the maximum extent to which the cups open is a function of the length of the cam follower opening and its angle with respect to the axis of the instrument.

Referring to FIG. 20, the axial movement of the drive member 580 is preferably controlled by a drive tube 586 in the form of a wire cable that is co-axial with the needle assembly control cable 508, both of which extend proximally to control elements in the handle assembly 20. In a particularly preferred embodiment, the drive tube 586 terminates at, and is permanently attached to a slide with finger grips or a spool member of the type known to the art. See, for example, FIGS. 1 and 15. Other means of controlling the movement of the cups 553, including those described above in connection with other embodiments of the invention can also be employed without effecting the utility of the overall advantages of the invention.

With continuing reference to FIG. 20, the needle assembly is slidably retained by its passage through central channel 596 in bypass 594. The bypass 594 also serves to determine the distal movement of the needle 511 by engaging the distal end or surface 502 of the needle stop member.

As best shown in the cross-sectional side view of FIG. 20, the drive member 580 is provided with opposing cam posts 582 that engage cam follower surfaces 584 in the cup arms 553. As will be explained in further detail below, when the drive member and its associated posts 582 are moved from a first position to a second position, the cam action causes the cups 555 to move from a closed to a fully-opened position. As will be understood by one of ordinary skill in the art, other cam follower surface arrangements can be provided to achieve the same result. For example, curvilinear and dual angled cam follower surfaces can be provided to change the rate of movement and forces applied to the cups for severing tissue samples.

The movement of the needle and the cups can be controlled independently by a thumb ring and slide linking member in a handle assembly, respectively, in a manner similar to that described above in connection with the method of operation of the prior embodiments. Distally facing surfaces of bypass member 594 and cup arms 553 form a sample contacting pusher surface that slides longitudinally relative to the needle 511 during a specimen ejection procedure and the sample is displaced down the needle to be dislodged at its distal end.

Referring to the embodiment 120 of FIG. 21, as in previously described embodiments, a thumb ring 122 is joined to the tail piece 606 of needle control assembly 500 by a flexible wire, wire tube or coil that extends through the interior of exterior cable 8. The thumb ring 122 is first joined to shaft 124 which slides in barrel 50. A push button 110 extends through barrel 50 and engages a needle release mechanism that, in turn, is joined to the co-axial flexible needle tube or coil 508.

With continuing reference to FIG. 21, a sliding spool or sleeve 121 with finger grips 123 is also mounted on the handle 52. The sliding sleeve 121 is attached via one or more wires or a co-axial tube whose axial movement opens and closes the cups via scissor mechanism described above, or by other means which will be described below.

Referring now to the cross-sectional view of FIG. 22, the needle control locking and release mechanism will be further described. The push button 110 is attached to a generally C-shaped resilient arm 112 that provides a biasing force that resist a downward force on button 110, thereby causing lock arm 114 to engage the proximal surface rim lock member 125 which is formed as part of thumb ring shaft 124. The tip 127 passes through close-fitting orifice 52 in barrel 50 and receives needle control wire 508 in secure attachment. Tip 127 terminates in proximal flange 126 and has mounted thereon spring 45. As illustrated in FIG. 22, the thumb ring is in the distally advanced position which compresses spring 45 between the end wall 54 of barrel 50 and flange 126, while lock arm 114 retains thumb ring shaft 124 by engaging rim lock 125. This illustration thus represents the operating position of the needle during the insertion, use and withdrawal of the needle biopsy forceps.

In order to disengage the samples from needle the cups are opened by advancing the sliding finger rings distally, positioning the cups over the sample collection container and then depressing the push button 110. Spring 45 moves the flange 126 proximally producing a corresponding movement of the needle 11.

In a further preferred embodiment of the handle assembly, the movement of the wire tube 588 attached to drive 580 is also controlled by a locking mechanism. A pair of adjacent opposing clamp members 360 are provided with oversize channels 362 to receive wire tube 588. Each clamp terminates in an external manual gripping element 364 that extends above the handle 52. Once the finger rings have been moved to open the cups, the user grips the elements 364 between thumb and forefinger and squeezes, thereby causing the clamps to move radially inward and frictionally engage the wire coil passing through the respective openings 362. Once this radial force is released, the frictional effect is dissipated and the cups can be closed by movement of the finger rings.

In a particularly preferred embodiment illustrated in FIGS. 21 and 22, a locking button is provided in the handle assembly. Before inserting the device into the working channel of the endoscope, the needle assembly 500 is locked in place with needle 511 positioned inside the cups by moving the thumb ring distally to compress spring 45 located in the handle. This action ratchets and displaces the handle as a result of the thumb ring travel; the button then snaps into the corresponding notch after the advance needle stop 502 makes contact with the distal bypass 594. The needle is in the extended position and contained within the closed cups.

The manual proximal control is preferably connected to the needle assembly by means of a flexible needle control tube, but other flexible connection means, such as a wire can also be used.

With further reference to FIG. 21, a slider positioned in the handle is connected by a flexible drive tube 588 to the drive member 580.

After one or more biopsy samples are mounted on the needle and severed, the cups are returned to the closed position and the assembly is withdrawn from the working channel of the endoscope. Once removed, the cups are positioned over a container of preservative solution, whereupon they are opened and the needle release button is depressed to cause the biasing spring to retract the needle, thereby dislodging the biopsy samples by contact with the distal bypass member 594. The engagement of the proximal portion of the needle stop with the interior shoulder 518 of the clevis 517 prevents the needle from passing through the channel 596 in the bypass member.

Other configurations of the safety ejection needle biopsy forceps within the scope of the present invention, including additional combinations of the embodiments illustrated and described above, alone or in conjunction with other features and elements known to the prior art, will be apparent to those of ordinary skill in the art. The method and apparatus of the invention is not limited for use in biopsy forceps, but can incorporated for use in other types of medical instruments in which the relative movement between a retaining needle containing one or more samples and a contacting surface is effective in dislodging samples from the needle. The scope of the invention is therefore to be determined with reference to the claims that follow.

I claim:

1. A needle biopsy instrument comprising:
   a hollow cable with a proximal and a distal end;
   two opposing cups operatively connected to said distal end of said hollow cable and moveable between an open configuration and a closed configuration, said cups, when in said closed configuration, defining a space between them for capturing at least one tissue sample severed by said cups;
   a needle disposed between said cups for piercing said at least one tissue sample, said needle being permanently operatively connected to said instrument, said needle being axially moveable so that said needle cannot extend beyond a most distal point of said space between said cups, axial movement of said needle being independent of the opening and closing of said cups;
   a tissue sample pushing surface disposed at a proximal end of said needle and engageable with said at least one tissue sample on the needle for movement relative to said needle so as to remove said at least one tissue sample from said needle upon retraction of said needle;
   a locking mechanism for locking said needle in a most advanced position wherein a most distal portion of said needle is disposed between said cups when said cups are in said closed configuration; and
   a needle advance stop mechanism for preventing said needle from advancing past said most advanced position relative to said cups when said cups are in said open configuration and when said cups are in said closed configuration,
   wherein the instrument is configured to eject said at least one tissue sample that has been pierced by said needle.

2. The needle biopsy instrument described in claim 1, wherein said needle is configured for stacking two or more tissue samples.

3. The needle biopsy instrument described in claim 2, wherein said two or more tissue samples, when stacked on said needle, are removed from said needle and ejected from said space between said cups when said needle is retracted from said space between said cups.

4. The needle biopsy instrument described in claim 1, wherein said needle is retractable from said space between said cups whether said cups are positioned in said open or said closed configuration.

* * * * *